(12) United States Patent
Cox et al.

(10) Patent No.: US 8,934,098 B2
(45) Date of Patent: Jan. 13, 2015

(54) FAST-INDEXING FILTER WHEEL AND METHOD OF USE

(75) Inventors: David Cox, Foster City, CA (US); Marc Haberstroh, San Jose, CA (US); Patrick Kinney, Hayward, CA (US); Albert Carrillo, Redwood City, CA (US); Jon Hoshizaki, Cupertino, CA (US); Maryam Shariati, Sunnyvale, CA (US); Howard King, Berkeley, CA (US); Joe Lee, Sunnyvale, CA (US); Matthew Chan, Palo Alto, CA (US)

(73) Assignee: Life Technologies Corporation, Carlsbad, CA (US)

( * ) Notice: Subject to any disclaimer, the term of this patent is extended or adjusted under 35 U.S.C. 154(b) by 384 days.

(21) Appl. No.: 12/873,132

(22) Filed: Aug. 31, 2010

(65) Prior Publication Data

US 2011/0128545 A1   Jun. 2, 2011

Related U.S. Application Data

(60) Provisional application No. 61/238,633, filed on Aug. 31, 2009, provisional application No. 61/238,667, filed on Aug. 31, 2009, provisional application No. 61/307,623, filed on Feb. 24, 2010, provisional (Continued)

(51) Int. Cl.
*G01N 21/25* (2006.01)
*C12Q 1/68* (2006.01)
(Continued)

(52) U.S. Cl.
CPC .......... *C12Q 1/6874* (2013.01); *B01F 13/0059* (2013.01); *B01F 13/0222* (2013.01);
(Continued)

(58) Field of Classification Search
CPC .......... C12Q 1/6874; C12Q 2563/107; G01N 21/6486; G01N 2021/6421
USPC .......................................................... 356/417
See application file for complete search history.

(56) References Cited

U.S. PATENT DOCUMENTS 3,796,887 A * 3/1974 Vincent et al. ................. 356/418
4,602,160 A * 7/1986 Mactaggart ..................... 356/73

(Continued)

FOREIGN PATENT DOCUMENTS

WO   WO-2011/026141   3/2011

OTHER PUBLICATIONS

Ludl Electronic Products Ltd Filter Wheels-High Performance Filter Changers for Quantitative Microscopy, Retrieved from the Internet ; URL:http://www.biovis.com/images;_Bio Vision Technologies, Feb. 19, 2005.

(Continued)

*Primary Examiner* — Kara E Geisel

(57) ABSTRACT

Various embodiments of a sequencing system capable of rapidly imaging samples at multiple wavelengths are provided herein. In one embodiment, the system includes a fast-indexing filter wheel having a plurality of excitation and emission filters capable of being rapidly rotated into and out of communication with an excitation source (e.g., an arc lamp, a laser. For example, the filter wheel can be configured to index in an amount of time falling within a range of about 40 ms to about 60 ms, preferably 50 ms. The system can also be configured to account for vibrations resulting from the quick starts and stops of the fast-indexing filter wheel as well as vibrations resulting from other sources. Various methods of rapidly imaging a sample at multiple wavelengths are also provided herein.

19 Claims, 22 Drawing Sheets

Related U.S. Application Data application No. 61/307,492, filed on Feb. 24, 2010, provisional application No. 61/307,641, filed on Feb. 24, 2010, provisional application No. 61/307,486, filed on Feb. 24, 2010.

(51) Int. Cl.

| | | |
|---|---|---|
| *B01F 13/00* | (2006.01) | |
| *B01F 13/02* | (2006.01) | |
| *B01J 19/00* | (2006.01) | |
| *B01L 3/00* | (2006.01) | |
| *G01N 35/00* | (2006.01) | |
| *G01N 35/10* | (2006.01) | |
| *G02B 21/34* | (2006.01) | |

(52) U.S. Cl.
CPC ......... *B01J19/0046* (2013.01); *B01L 3/50273* (2013.01); *G01N 35/00069* (2013.01); *G01N 35/1002* (2013.01); *B01J 2219/00317* (2013.01); *B01J 2219/00466* (2013.01); *B01J 2219/00527* (2013.01); *B01J 2219/00576* (2013.01); *B01J 2219/00596* (2013.01); *B01J 2219/00648* (2013.01); *B01J 2219/00659* (2013.01); *B01J 2219/00722* (2013.01); *B01L 3/502707* (2013.01); *B01L 2200/027* (2013.01); *B01L 2200/0647* (2013.01); *B01L 2200/0684* (2013.01); *B01L 2200/16* (2013.01); *B01L 2300/0819* (2013.01); *B01L 2300/0822* (2013.01); *B01L 2300/0867* (2013.01); *B01L 2300/0877* (2013.01); *B01L 2300/0887* (2013.01); *B01L 2300/1822* (2013.01); *B01L 2400/0427* (2013.01); *G01N 35/1097* (2013.01); *G01N 2035/00148* (2013.01); *G01N 2035/00237* (2013.01); *G01N 2035/1034* (2013.01); *G02B 21/34* (2013.01)
USPC .......................................... 356/417; 356/418

(56) References Cited

U.S. PATENT DOCUMENTS

| | | | | |
|---|---|---|---|---|
| 4,648,714 | A | * | 3/1987 | Benner et al. ................. 356/301 |
| 4,945,250 | A | * | 7/1990 | Bowen et al. ............. 250/461.1 |
| 5,149,972 | A | * | 9/1992 | Fay et al. ................... 250/461.1 |
| 6,075,643 | A | * | 6/2000 | Nonoda et al. ................ 359/385 |
| 6,414,805 | B1 | * | 7/2002 | Reichman et al. ............ 359/889 |
| 6,440,664 | B1 | * | 8/2002 | Digby et al. ............... 422/82.08 |
| 2002/0051992 | A1 | * | 5/2002 | Bridgham et al. ................ 435/6 |
| 2002/0085293 | A1 | * | 7/2002 | Stuckey ....................... 359/831 |
| 2004/0001196 | A1 | * | 1/2004 | Shibazaki et al. ............ 356/129 |
| 2005/0151972 | A1 | * | 7/2005 | Boege et al. ................. 356/417 |
| 2006/0012860 | A1 | * | 1/2006 | Bender ........................ 359/381 |
| 2007/0195321 | A1 | * | 8/2007 | Soussaline et al. ........... 356/318 |

OTHER PUBLICATIONS

PCT/US2010/047402 International Preliminary Report on Patentability, Mar. 2012.
PCT/US2010/047402 International Search Report, Feb. 2011.
PCT/US2010/047402 Written Opinion, Feb. 2011.

\* cited by examiner

FAST-INDEXING FILTER WHEEL AND METHOD OF USE

RELATED APPLICATIONS

This application claims priority pursuant to 35 U.S.C. §119 (e) to U.S. Provisional Patent Application Ser. No. 61/238,633, filed on Aug. 31, 2009, entitled "Enhanced Systems and Methods For Sequence Detection," U.S. Provisional Patent Application Ser. No. 61/238,667, filed on Aug. 31, 2009, entitled "Enhanced Flowcell and Reagent Delivery For Sequence Detection," U.S. Provisional Patent Application Ser. No. 61/307,623, filed on Feb. 24, 2010, entitled "Methods of Bead Manipulation and Forming Bead Arrays," U.S. Provisional Patent Application Ser. No. 61/307,492, filed on Feb. 24, 2010, entitled "Flowcells and Methods of Filling and Using Same," U.S. Provisional Patent Application Ser. No. 61/307,641, filed on Feb. 24, 2010, entitled "Flowcells and Methods of Filling and Using Same," and U.S. Provisional Patent Application Ser. No. 61/307,486, filed on Feb. 24, 2010, entitled "Flowcell, Flowcell Delivery System, Reagent Delivery System, and Method For Sequence Detection," the entirety of each of these applications being incorporated herein by reference thereto.

FIELD

The present disclosure is directed towards molecular sequencing, in particular towards enhanced imaging mechanisms.

BACKGROUND

Nucleic acid sequencing techniques are of major importance in a wide variety of fields ranging from basic research to clinical diagnosis. The results available from such technologies can include information of varying degrees of specificity. For example, useful information can consist of determining whether a particular polynucleotide differs in sequence from a reference polynucleotide, confirming the presence of a particular polynucleotide sequence in a sample, determining partial sequence information such as the identity of one or more nucleotides within a polynucleotide, determining the identity and order of nucleotides within a polynucleotide, etc.

Next generation sequencing techniques commonly utilize fluidic technologies for performing aspects of sample analysis. For example, Assignee's PCT Application Publication No. WO 2006/084132, entitled "Reagents, Methods, And Libraries for Bead-Based Sequencing," the entirety of which is incorporated herein by reference thereto, provides various techniques, systems, and methods for sequencing a sample coupled to a solid-support (e.g., a bead, particle, surfaces and surface features, etc.) wherein a plurality of supports are disposed over the surface of a flowcell. Flowcells allow for a large number of samples, or samples coupled to other solid-supports, to be immobilized in random and/or ordered fashion across reaction chamber(s) while reagents are added to, removed from, or pumped through the chamber(s) to produce the desired effect (e.g., reaction, wash, etc.). Typical systems can also include imaging, optics, or other detection components in communication with the reaction chambers thereby allowing sample images or other properties to be rapidly captured and analyzed.

In view of the ever-increasing benefits of genomic analysis, demand continues for, among other things, faster sample analysis, higher throughput, enhanced sequence accuracy, and reduced cost (e.g., on a per-run or per-genome basis).

SUMMARY

Various embodiments of a detection system capable of rapidly imaging a sample at multiple wavelengths are provided herein. In some embodiments, systems having an excitation source (e.g., an arc lamp, laser, a LED, an incandescent lamp, RF lamp, chemiluminescence, etc.) configured to irradiate a target sample(s), a fast-indexing filter wheel having a plurality of filters capable of being rapidly indexed into optical communication with the excitation source are provided. The systems can also include various embodiments of a motor coupled to the fast-indexing filter wheel, and configured to rapidly index between filters (e.g., in between about 40 ms and about 60 ms, between about 45 ms and about 55 ms, about 50 ms, etc.).

The fast-indexing filter wheel can be configured to include any number of filters. For example, the filter wheel can include at least 4 filters, 5 or more filters, etc. The fast-indexing filter wheel can further be configured to include both excitation and emission filters. That is, in some embodiments, the wheels can include at least one emission filter corresponding to at least one excitation filter. In some embodiments, the fast-indexing filter wheel further includes a plurality of emission filters, each emission filter corresponding to one of the excitation filters. In one embodiment, each emission filter can be mounted onto the filter wheel so as to be substantially perpendicular relative to the corresponding excitation filter.

In some embodiments, the filter wheel can include filters configured for a single excitation wavelength and multiple emission wavelengths, multiple excitation wavelengths and multiple emission wavelengths, multiple excitation wavelengths and a single emission wavelength, and multiple bandpass regions on any of the above filters. Any of these combinations can be mounted on a single filter wheel or on separate filter wheels.

Various embodiments of the system can also be configured to account for or reduce vibrations resulting for the rapid starting and stopping of the filter wheel. For example, the filter wheel can be coupled to an anti-vibration mechanism configured to reduce any such interfering vibrations. In one embodiment, the anti-vibration mechanism is a counter-balance fly-wheel mechanism.

Various embodiments of a fast-indexing filter wheel are also provided herein. In some embodiments, the filter wheels can be rotatably coupled to a frame or support. The wheels can further include a plurality of filters (e.g., excitation filters) incorporated therein such that each of the filters can be placed into optical communication with an excitation source. The fast-indexing wheel can also be coupled with a motor so as to allow the wheel to rapidly index between filters (e.g., in an amount of time between about 40 ms and about 60 ms, between about 45 ms and about 55 ms, about 50 ms, etc.).

Various methods of analyzing a sample are also provided herein. For example, in some embodiments, the methods include providing a fast-indexing filter wheel having a plurality of filters (e.g., excitation filters), positioning a first filter of the plurality into optical communication with an excitation source, and irradiating an area of a sample with excitation energy such that a first emission signal is generated. The method can also include indexing a second filter of the plurality into optical communication with the excitation source, and irradiating the area of the sample with a second excitation energy from the excitation source such that a second emission signal is generated. Once the sample or area of sample has been rapidly imaged at multiple wavelengths, the method can further include moving the sample relative to the fast-moving filter wheel such that another area of the sample is positioned to be irradiated by at least the first excitation energy. In other embodiments, the optics and detection mechanism can move while the sample remains stationary.

In some embodiments, methods can include repeating the first irradiating step, the indexing step, and the second irradiating step for each of the plurality of filters (e.g., 2, 3, 4, 5, 6, etc.) prior to moving the sample such that additional areas of the sample (or other imaging panels) can be interrogated. In some embodiments, methods can further include detecting each of the emission signals corresponding to each of the plurality of filters for the area of the sample (or imaging panel) prior to analyzing any other area of the sample (or other imaging panel). The method can further include repeating all such steps until the entire sample (or at least those areas of interest) has been analyzed.

The method can include rapidly indexing between filters thereby allowing for multiple images of a single sample to be taken at multiple wavelengths almost simultaneously. For example, in one embodiment, the fast-indexing filter wheel can index between filters in an amount of time in a range of between about 40 ms and about 60 m, between about 45 ms and about 55 ms, about 50 ms, etc.

Various embodiments of a method of imaging a biomolecule sample are also provided herein. For example, the method can include providing an apparatus rotatably coupled to a fast-indexing filter wheel having a plurality of filters incorporated therein, positioning an area of a flowcell into optical communication with a first filter of the plurality, and irradiating the area of the flowcell (e.g., imaging panel) with excitation energy emanating from a first filter. The method can also include indexing the fast-indexing filter wheel such that a second filter is in optical communication with the area of the sample and irradiating the area with excitation energy emanating from the second filter. In some embodiments, the method can also include repeating the indexing and irradiating steps for each of the plurality of filters, and moving the flowcell (or moving the detection assembly relative to the flowcell) such that a second area of the sample is moved into optical communication with at least one of the filters.

In some embodiments, the method can include repeating the irradiating, indexing, and irradiating steps for the second area. Additionally, methods can also include moving the flowcell such that a third area of the sample is moved into optical communication with at least one of the excitation filters. These steps can be repeated until the entire area (or at least the desired area) of the sample has been analyzed.

Instructions for performing or implementing the various functions and features described above and in the remainder of this disclosure can be embodied in hardware, firmware, software, or combinations thereof. Instructions can also be contained in computer-readable media, and optionally be transferable between different systems and reconfigurable and updatable via on-line services, by the user, or by other processes and means.

These and other embodiments are described in greater detail below.

BRIEF DESCRIPTION OF THE DRAWINGS

The present disclosure will be more fully understood from the following detailed description taken in conjunction with the accompanying drawings, in which.

DETAILED DESCRIPTION

Figure 1:
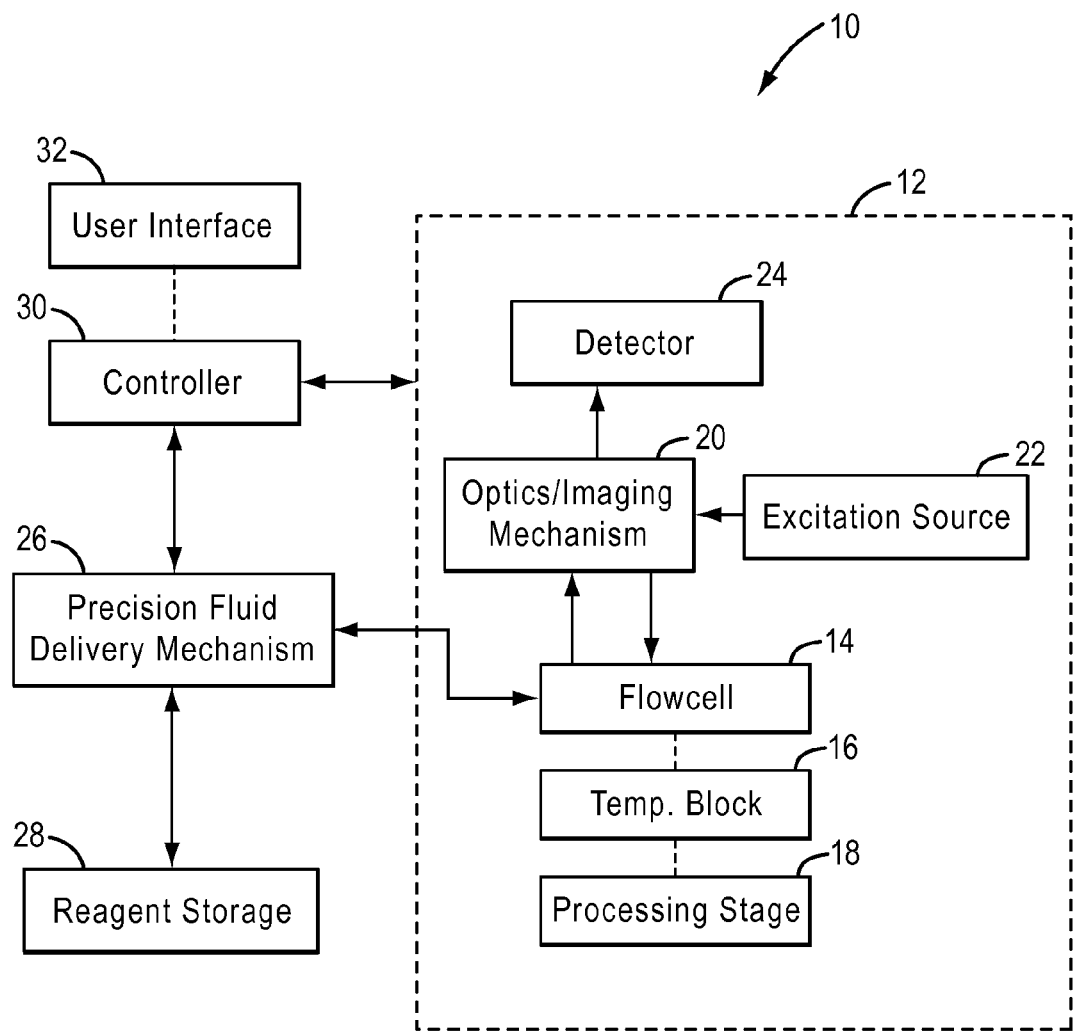
FIG. 1 is an overview of a preferred embodiment of the presently disclosed sequencing system.

Various embodiments of an analysis system capable of rapidly imaging samples at multiple wavelengths are provided herein. Such a system may be desirably adapted for use with a biological analysis instrument such as a nucleic acid sequencing apparatus. In use, the enhanced imaging mechanism allows for a sample (or a portion thereof) to be rapidly interrogated at multiple wavelengths prior to analyzing another sample (or another area of the sample) thereby increasing system efficiency and reducing data storage requirements. That is, as the sample can be interrogated at desired wavelengths in a serial manner or almost simultaneously, the system does not need to be configured to store vast quantities of image data at each of the wavelengths which are subsequently compared after imaging is complete but rather image analysis may proceed "on the fly" for each image panel. Additionally, in interrogating the entire sample, the system can be configured such that if the sample has multiple imaging panels, the sample can be translated and the detection system be stationary or the sample can be stationary and the entire detection system be translated.

Various embodiments of a fast-indexing filter wheel configured to enhance the system's ability to image at multiple wavelengths are provided herein. The fast-indexing filter wheel includes a plurality of excitation filters capable of being rapidly rotated into and out of communication with an excitation source (e.g., an arc lamp, a laser, a LED, an incandescent lamp, RF lamp, chemiluminescence, etc.). Additionally, the fast-indexing filter wheel can be configured to rapidly settle as a new excitation filter is positioned into communication with the excitation source. Rapid settling is important to reduce the overall analysis time because of the time saved in each imaging panel operation which adds up to significant percentage of time for imaging. Without settling, undesirable image blurring or distortion may result. In addition to the rapid indexing time, this quick settling further enhances image quality while also reducing analysis time. The system can also be configured to account for vibrations resulting from the quick starts and stops of the fast-indexing filter wheel as well as vibrations resulting from other sources.

The analysis systems, optics, imaging, software, and other systems, apparatuses, and methods disclosed herein can be used in connection with various sequencing techniques and processes, such as chain termination or dideoxynucleotide sequencing, chemical degradation sequencing, sequencing by synthesis, pyrosequencing, sequencing by hybridization, oligonucleotide-based sequencing, and single-molecule sequencing. The analysis systems, flowcells, fluid and reagent delivery systems, software, and other systems, apparatuses, and methods disclosed herein can also be used in connection with automated, partially automated, and manual sequencing instruments and processes. For example, low-volume flowcells disclosed herein can be used for performing next-generation sequencing reactions such as oligonucleotide-based reactions and sequencing-by-synthesis reactions. An advantage of some embodiments of the disclosed flowcells is a reduction in the amount of sample or reagent that is used; where such samples or reagents are available only in small quantities or are expensive or otherwise difficult to make or acquire, substantial reduction in cost can be realized (sequencing of a whole genome for $1,000 or less) and the sequencing of samples that were previously difficult or impossible to sequence.

Certain exemplary embodiments will now be described to provide an overall understanding of the principles of the structure, function, manufacture, and use of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

FIG. 1 provides an overview of a preferred embodiment of the presently disclosed sequencing system 10. As shown, the system 10 can include an analysis apparatus 12 in communication with a reagent delivery mechanism 26. Additionally, the analysis apparatus 12 (and any or all of the components thereof) and the reagent delivery mechanism 26 can be in communication with a controller (e.g., a computer/processor) capable of, as detailed below, controlling various aspects of the apparatus 12 (e.g., the fast-indexing filter wheel) and delivery mechanism 26, implementing various steps, storing data, performing analysis, etc. The controller is further in communication with a user interface 32.

The sequencing apparatus 12 can include a wide variety of components. While FIG. 1 presents numerous components as being part of the apparatus 12, it will be understood that the apparatus may not include all of these components or may include some additional components not included herein. Additionally, any or all of these components may be considered to be independent of the apparatus 12. All such variations are within the spirit and scope of the present disclosure.

In the preferred embodiment, the apparatus 12 includes a sample chamber or flowcell 14 in communication with a temperature block 16 and processing stage 18. The flowcell 14 can be configured to retain sample in any number of discrete reactions chambers. The reaction chambers can likewise be sized and configured to minimize an amount of reagent volume required to affect the desired result within each chamber, That is, the width, length, and/or height of the chamber can be selected to maintain desired flow characteristics while ensuring the desired reaction takes place. Additionally, the discrete chambers allow for multiple, distinct reactions or distinct samples to be analyzed simultaneously, Thus, an entire flowcell 14 does not need to be utilized when a single chamber (e.g., 1 of 6 available chambers) can provide the desired result. Preferred embodiments of a flowcell 14, temperature block 16, processing stage 18, and reagent delivery mechanism 26 for use with the presently disclosed system are disclosed in applicants' co-pending U.S. patent application Ser. No 12/873,190, filed on Aug. 31, 2010, entitled "Low-Volume Sequencing System and Method of Use," the entirety of which is incorporated herein by reference thereto.

Once mounted to a processing stage 18 and ready for analysis and imaging, the flowcell and associated sample disposed therein can be placed into communication with an embodiment of an optics/imaging mechanism 20. As detailed below, in various embodiments the optics/imaging mechanism 20 is configured to filter excitation energy from an excitation source (e.g., an arc lamp, a laser, a LED, an incandescent lamp, RF lamp, chemiluminescence, etc.) through two or more filters such that each sample (or selected area of the flowcell) is imaged using a plurality of wavelengths prior to indexing or moving on to the next sample (or area of the flowcell). The optics/imaging mechanism 20 can further be configured to include a plurality of emission filters (detailed below) corresponding to each of the excitation filters such that each of the plurality of emission signals pass through a corresponding emission filter prior to falling on the detector 24 (e.g., a CCD).

In a preferred embodiment, the optics/imaging mechanism 20 includes a fast-indexing filter wheel rotatably mounted within the system and holding the plurality of filters required to perform the desired analysis. In use, the filter-wheel can be configured to rapidly index between filters in about 40 ms to about 60 ms, within a range of about 45 ms and about 55 ms, or about 50 ms. The ability to quickly index and settle so as to be ready for imaging the sample at a second (or third, fourth, etc.) wavelength provides the system with the ability to quickly image each sample or sample area at a plurality of distinct wavelengths prior to moving on to another sample or sample area. In view of the quick indexing and setting time, the system can be considered to image each target area at multiple wavelengths almost simultaneously.

As detailed below, various configurations of the presently disclosed fast-indexing filter wheel are within the spirit and scope of the present disclosure. For example, the filter wheel can include filters configured for a single excitation wavelength and multiple emission wavelengths, multiple excitation wavelengths and multiple emission wavelengths, multiple excitation wavelengths and a single emission wavelength, and multiple bandpass regions on any of the above filters. Any of these combinations can be mounted on a single filter wheel or on separate filter wheels.

Figure 2:
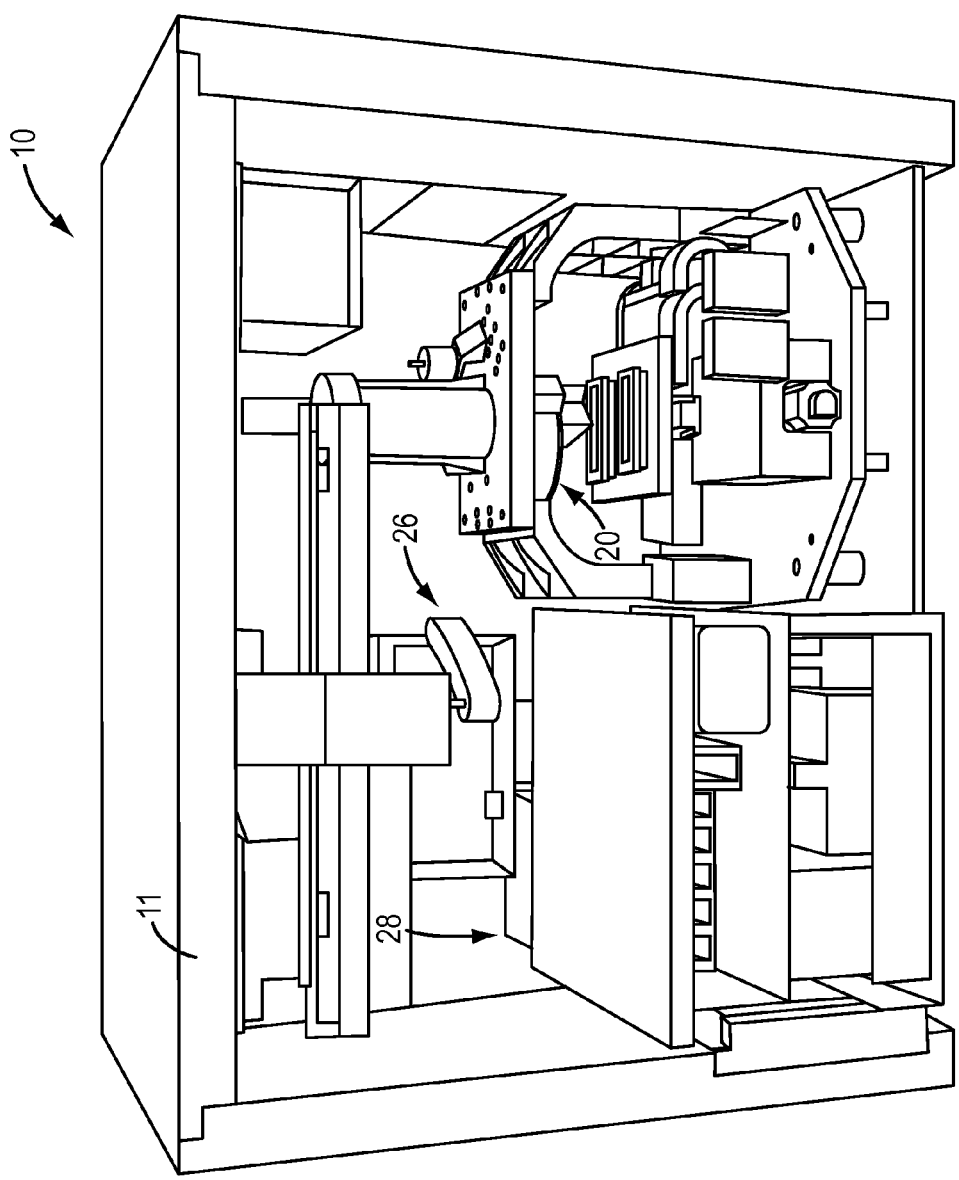
FIG. 2 is a representation of the sequencing system of FIG. 1.
Figure 3:
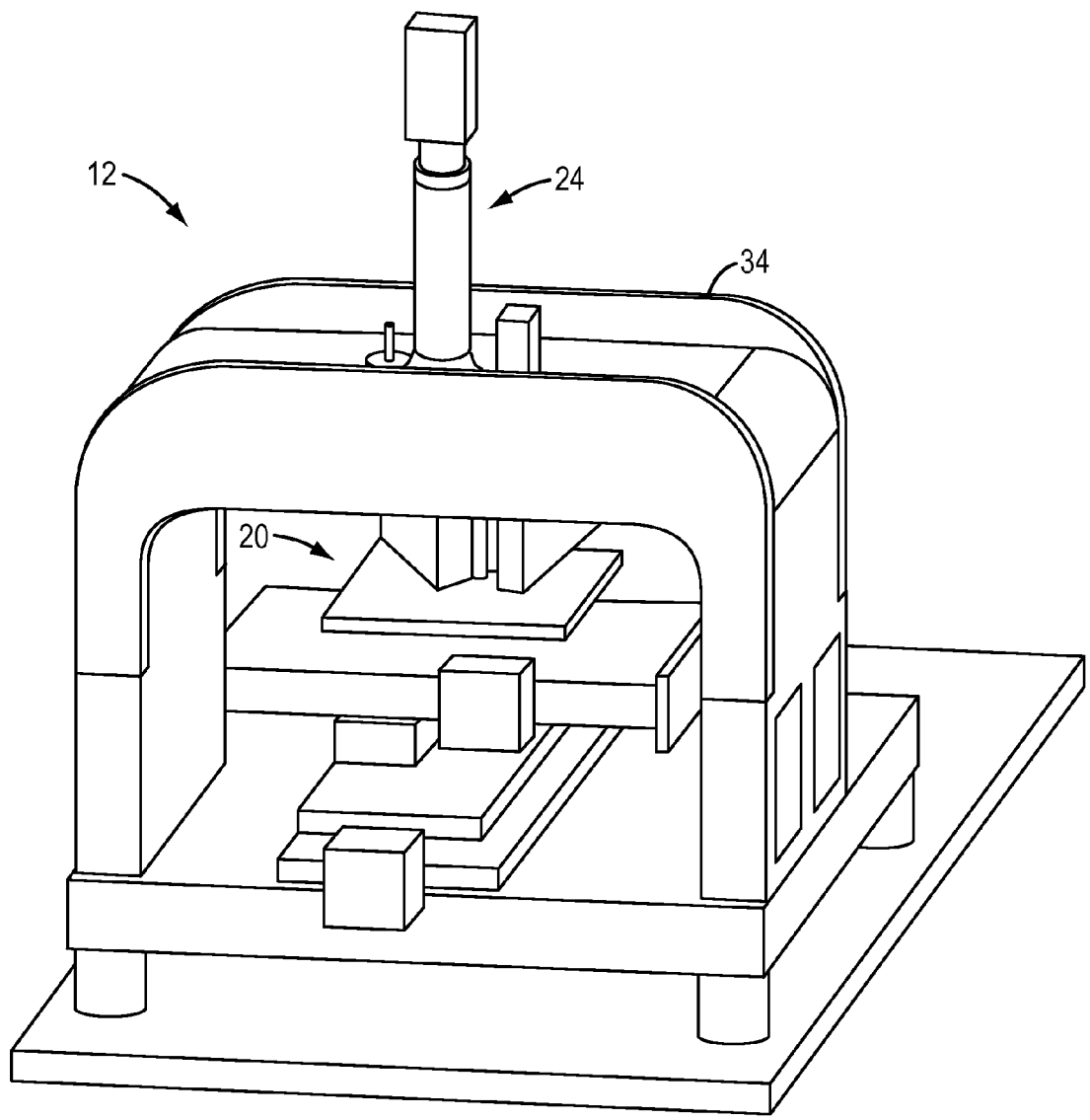
FIG. 3 is a representation of the presently disclosed sequencing apparatus.
Figure 4:
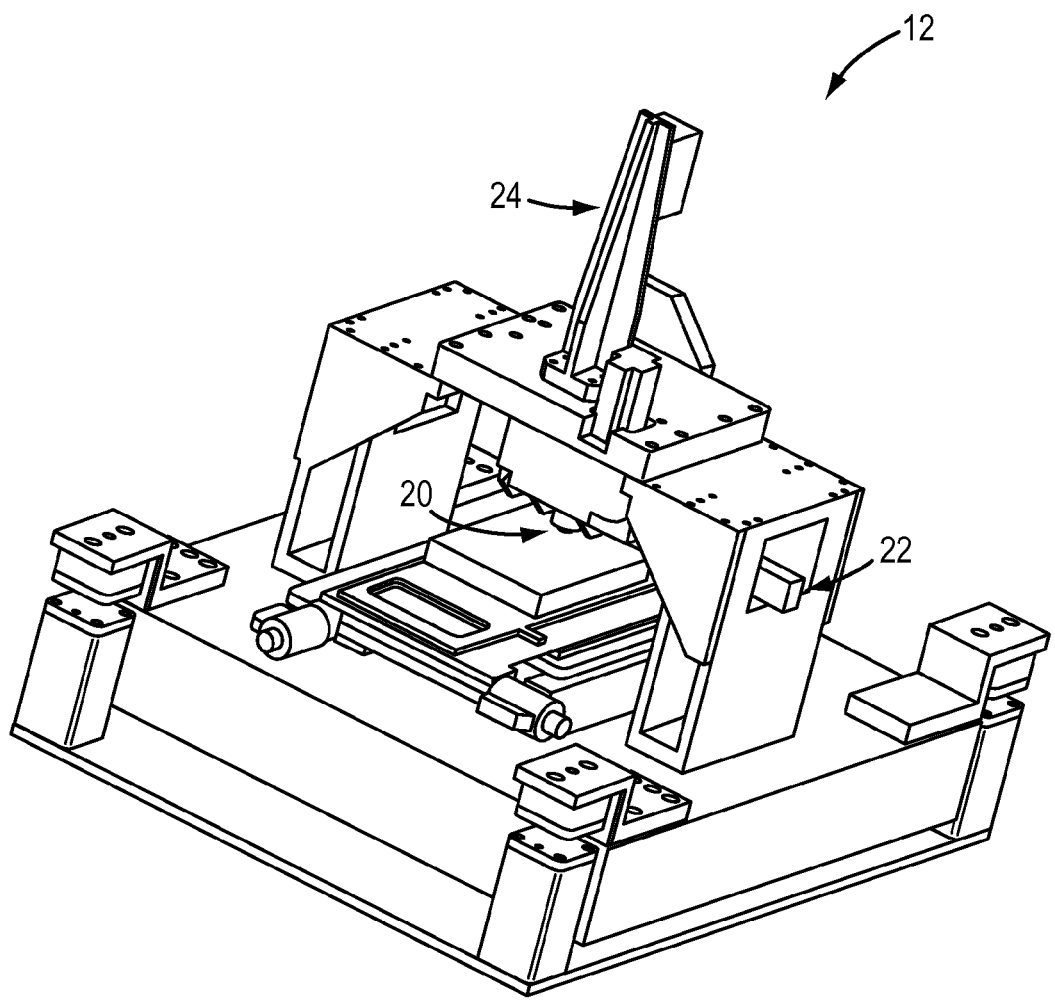
FIG. 4 is another representation of the sequencing apparatus of FIG. 3.

FIGS. 2-4 provide various representations of an embodiment of the sequencing system 10 and apparatus 12. That is, FIG. 2 shows an embodiment of an instrument shell 11 housing the system apparatus 12, the optics/imaging mechanism 20 (including the fast-indexing filter wheel), the precision fluid delivery mechanism 26, etc. As shown, the apparatus 12 can include the detector 24 and imaging/optics mechanism 20 disposed in communication with the flowcell 14 while the reagent delivery mechanism 26 and reagent storage container 28 are positioned adjacent the apparatus 12. Various sizes and configurations of the instrument shell 11 are within the spirit and scope of the present disclosure. For example, the shell 11, apparatus 12, and reagent delivery mechanism 26 can be sized and configured to be positioned on a lab-bench. Those skilled in the art will appreciate that any scale of the system 10 is within the spirit and scope of the present disclosure.

FIG. 3 is another representation of the apparatus 12 showing various components coupled to a frame 34. The frame 34 can provide for stability as well capable of maintaining a desired relationship between components. For example, the detector 24 and optics/imaging mechanism 20 can be coupled to the frame 34 such that flowcells can be moved into and out of communication with these components.

FIG. 4 provides another representation of the apparatus 12 with various components removed for clarity. As shown, the processing stage 18 can be coupled to a motor (not shown) such that the stage 18 can be moved between a sample (e.g., flowcell) loading position (as shown) and an analysis position disposed in communication with the optics/imaging mechanism 20. FIG. 4 also provides an embodiment of the relationship between the excitation source 22, the optics/imaging mechanism 20, and detector 24. As shown, the excitation source 22 and optics/imaging mechanism 20 can be positioned above the flowcell 14. However, in other embodiments, the source 22 and mechanism 20 can be positioned below the flowcell 14.

Figure 5:
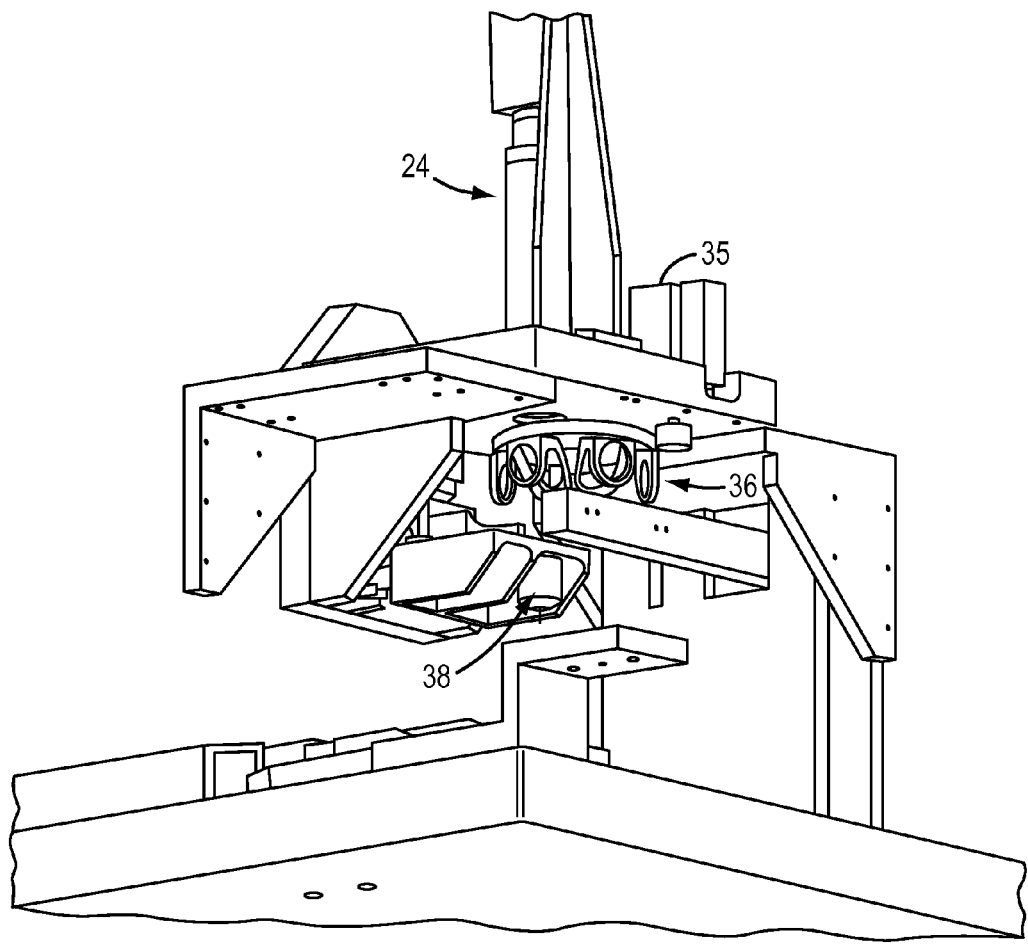
FIG. 5 is a perspective view of a preferred embodiment of the presently disclosed fast-indexing filter wheel.

FIGS. 5-9 provide views of a preferred embodiment of the presently disclosed optics/imaging module 20. Referring to FIG. 5, the optics/imaging mechanism 20 includes a fast-indexing filter wheel rotatably coupled to a stabilization plate 35. The optics/imaging mechanism 20 can also include an objective lens 38 coupled to a z-direction controllable carriage (not shown). FIG. 5 also provides an embodiment of a detector 24 disposed above the stability plate 35. Those skilled in the art will appreciate that various spatial relationships between such components are within the spirit and scope of the present disclosure.

The fast-indexing filter wheel can be configured to rapidly index a plurality of excitation filters into and out of communication with an excitation source, and can also be configured to rapidly settle at each new location thereby significantly increasing system efficiency. Various embodiments of the fast-indexing filter wheel are within the spirit and scope of the present disclosure. Additionally, the fast-indexing filter wheel can be oriented relative to other components of the system in various manners.

Figure 6:
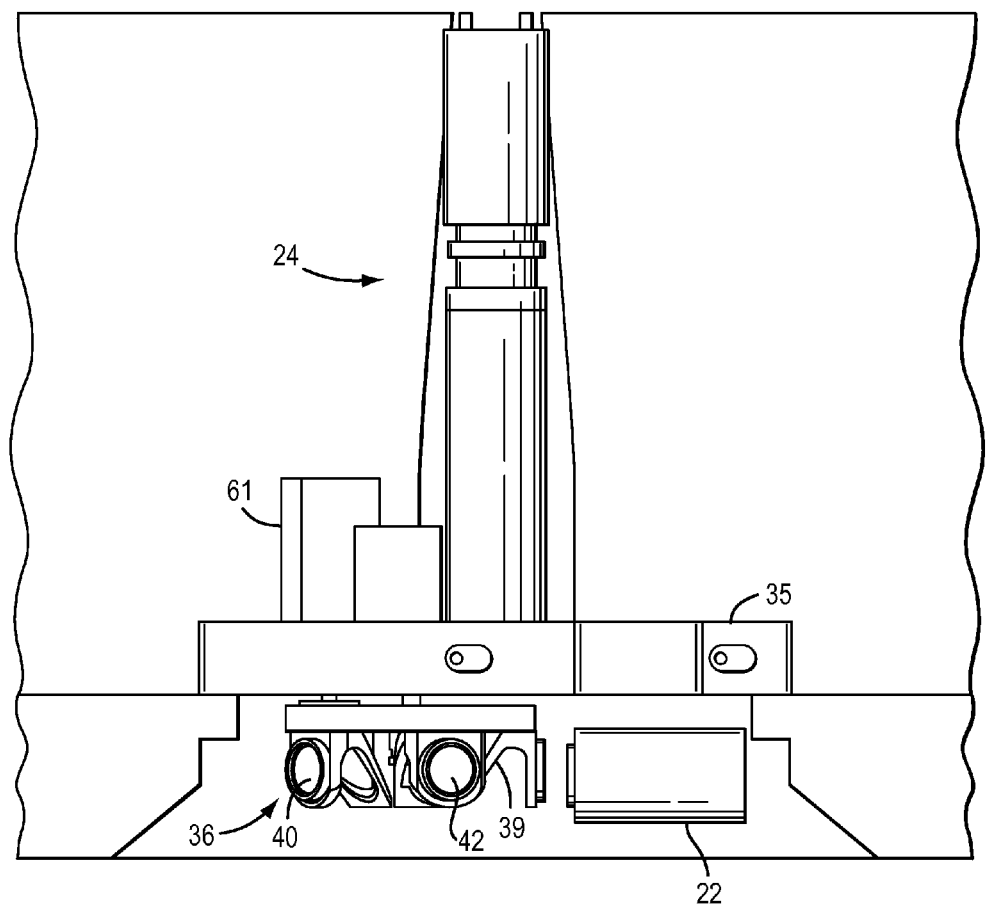
FIG. 6 is a side view of the fast-indexing filter wheel of FIG. 5.

FIG. 6 provides a preferred embodiment of the fast-indexing filter wheel 36 positioned in relation to the excitation source 22. That is, at an arbitrarily selected or desired "initial position," a first excitation filter of the filter-wheel can be positioned adjacent the excitation source 22 such that the first excitation filter is in optical communication with the excitation source 22. That is, the first excitation filter can be positioned such that excitation energy from the excitation source 22 is directed through the first excitation filter en route to the sample. While the excitation filter can be positioned in various orientations relative to the excitation source 22, in one embodiment, the filter-wheel 36 is configured such that the first excitation filter is substantially perpendicular to the excitation source 22. In this configuration, the excitation source 22 can deliver excitation energy through the first filter and into other optical elements such as a dichroic element held by a dichroic holder 39 configured to direct the desired energy towards the target sample.

Any number of excitation filters can be incorporated into the fast-indexing filter wheel. For example, in fluoro-genetic analytic methods such as analyzing polynucleotides, systems typically require images taken at multiple distinct wavelengths which discern between different types of tagged or labeled molecules. For example, four tags (e.g., fluorophores) may be configured to emit discrete emission signals with distinct excitation energies corresponding to the four nucleotide bases present within a nucleic acid strand or fragment. Thus, in one embodiment, the fast-indexing filter wheel can be configured to include at least four excitation filters. In a preferred embodiment, as shown in FIGS. 6-9, the fast-indexing filter wheel includes 5 excitation filters 40, 42, 44, 46, 48 wherein these filters allow for a sample to be imaged at least 4 distinct wavelengths (e.g., corresponding to 4 fluorophores representative of distinct nucleotides) while a fifth filter can be provided as a standard or reference. Additionally, the filter wheel can be configured to retain the plurality of excitation filters 40, 42, 44, 46, 48 such that each filter can be rotated into optical communication with the excitation source.

Figure 7:
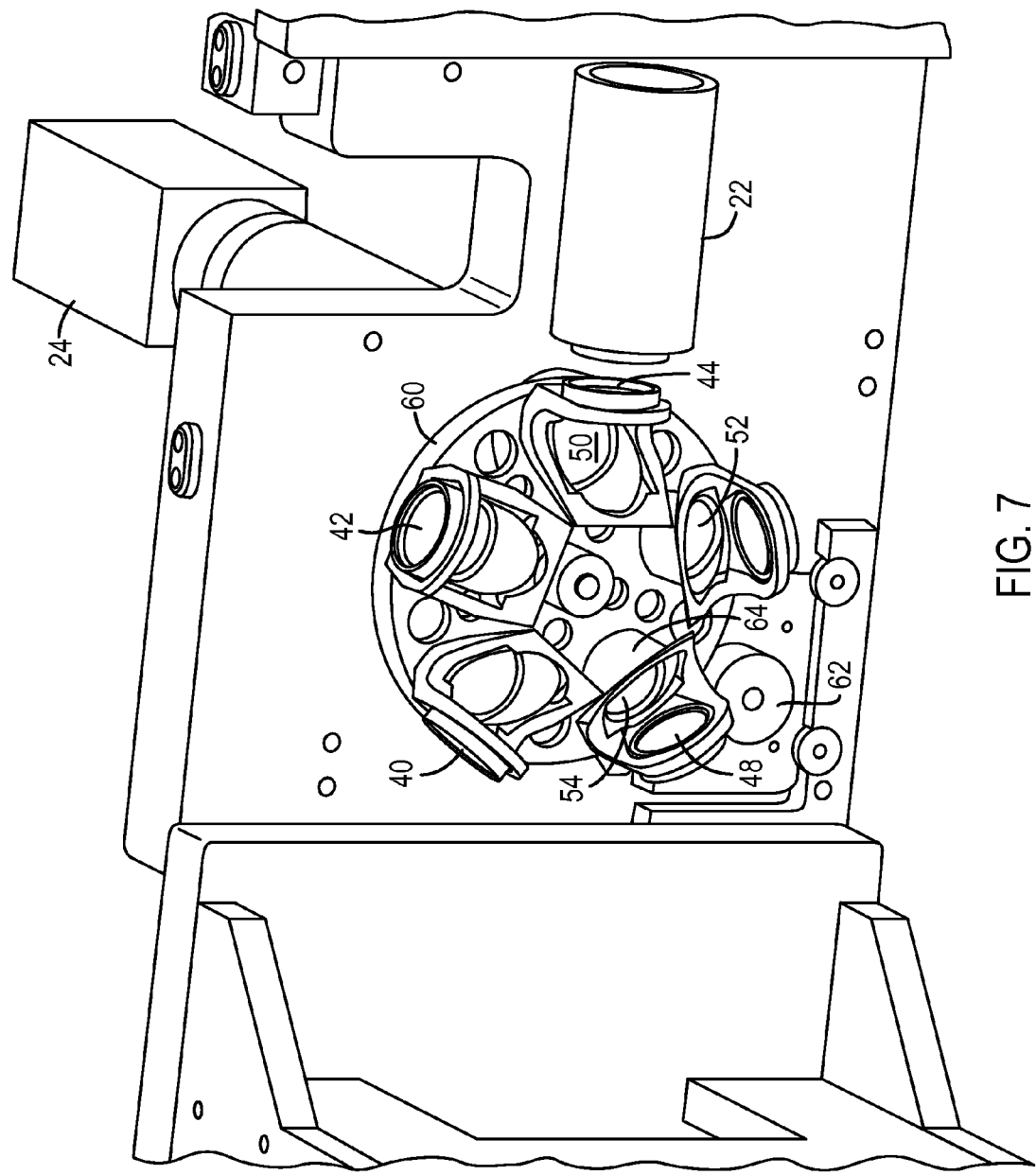
FIG. 7 is another view of the fast-indexing filter wheel of FIG. 5.
Figure 8:
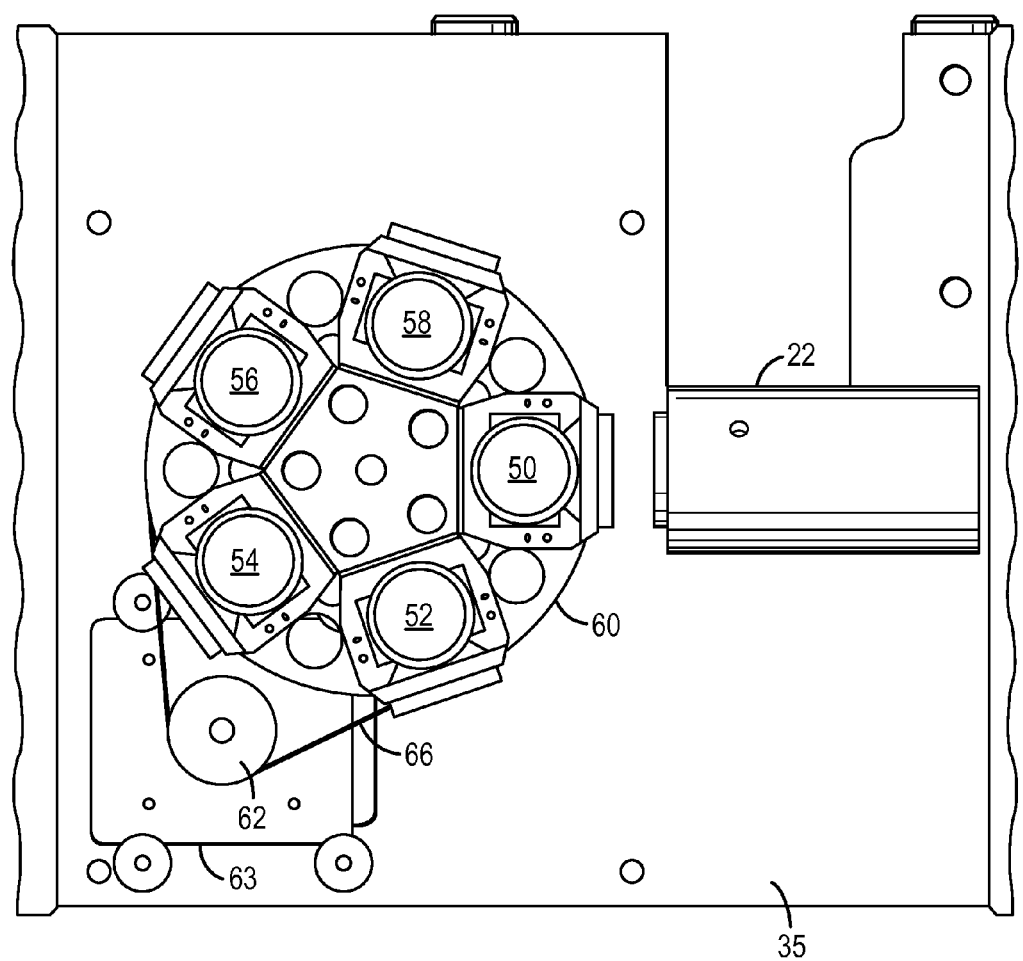
FIG. 8 is a bottom view of the fast-indexing filter wheel of FIG. 5.
Figure 9:
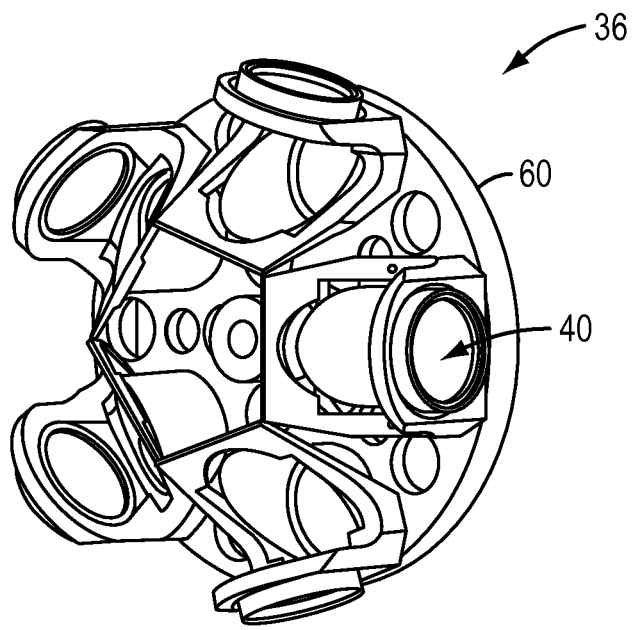
FIG. 9 is a perspective view of a preferred embodiment of the fast-indexing filter wheel.

In a preferred embodiment, the fast-indexing filter wheel can also be configured to retain a plurality of emission filters in addition to the plurality of excitation filters. For example, as shown in FIGS. 7-9, the fast-indexing filter wheel 36 includes a plurality of emission filters 50, 52, 54, 56, 58 configured to receive emission signals emitted from the target sample en route to the detector 24. The excitation 40, 42, 44, 46, 48 and emission filters 50, 52, 54, 56, 58 can be incorporated into the fast-indexing filter wheel 36 in various manners. For example, in a preferred embodiment, as best shown in FIG. 7 and FIG. 9, the filter wheel 36 is configured such that each excitation filter 40 is substantially perpendicular to each corresponding emission filter 50. Thus, as the excitation filter 40 is positioned within the optical path of the excitation source, the corresponding emission filter 50 can be positioned into communication with the sample such that an emission signal passes through the emission filter. Those skilled in the art will appreciate that various filter wheel configurations are within the spirit and scope of the present disclosure including the use of multiple filter wheels (e.g., one excitation filter wheel and one emission filter wheel).

The filter-wheel 36 can be configured to contain any number of emission filters. In a preferred embodiment, the filter wheel 36 includes a number of emission filters 50, 52, 54, 56, 58 corresponding to the number excitation filters 40, 42, 44, 46, 48. That is, as a first excitation filter 40 is positioned to receive excitation energy from an excitation source 22, a corresponding first emission filter 50 is simultaneously positioned to receive the resulting emission energy emitted from the sample. Once this image has been captured, the fast-indexing filter wheel 36 can index to a second position wherein a second excitation filter 42 is positioned into optical communication with the source 22, while a second emission filter 52 is positioned to receive a second emission signal emitted from the sample. These steps can be repeated until each of the excitation and corresponding emission filter(s) 40, 50 have been moved into communication with the excitation source 22. After an image has been captured at each of the distinct wavelengths due to the use of these distinct filters, the sample/flowcell or optics/imaging module can be moved such that a second sample or second area of the sample can be imaged at each of the distinct wavelengths. These steps can be repeated until the entire area or at least all desired areas of the sample have been analyzed.

As indicated above, the fast-indexing filter wheel can be configured to index between filters at a rapid rate thereby allowing multiple images to be taken at distinct wavelengths almost simultaneously. For example, in one embodiment, the fast-indexing filter wheel can index between filters in an amount of time within a range of between about 40 ms and 60 ms, or between about 45 ms and 55 ms. In a preferred embodiment, the indexing time is about 50 ms.

Figure 10:
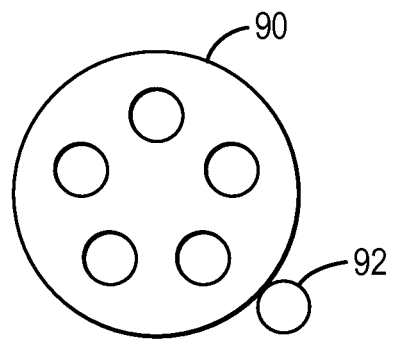
FIG. 10 is a representation of an embodiment of a filter wheel coupled to a motor.

As shown in FIGS. 6 and 8, the optics/imaging mechanism 20 can include a motor 63 disposed within a motor casing 61 for driving the fast-indexing filter wheel 36. For example, the filter wheel can be rotated by a motor that is gear reduced or timing belt reduced so it can be rotated by a small motor with a low inertia. The assembly can be made from and/or comprise a variety of materials, including but not limited to, titanium or carbon fiber. The filter assembly can also be configured with little or no nonessential material to make it very light. FIG. 8 provides an example wherein the small and large gears 62, 60 are coupled via a timing belt 66, and FIG. 10 provides an example wherein a small gear 92 drives a large gear 90 by directly engaging the large gear 90.

Figure 11A:
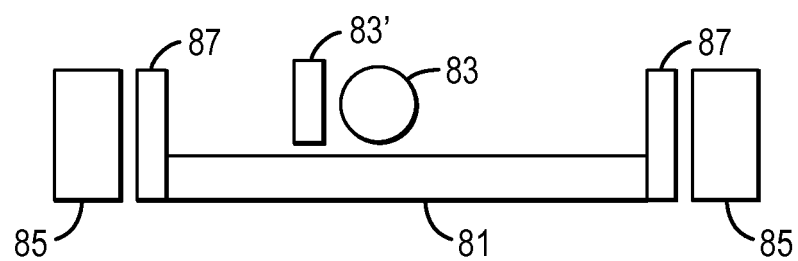
FIG. 11A is a preferred embodiment of a filter-wheel motor.

In a preferred embodiment, the filter-wheel can be coupled to a light-weight motor configured to rapidly index the filter wheel with minimal vibration. FIG. 11A provides a preferred embodiment of such a motor. As shown, a filter wheel 81 having multiple filters 83, 83' can be coupled to magnets 87 and positioned relative to electric coils 85. In some embodiments, the electric coils and magnets can be reversed.

Figure 11B:
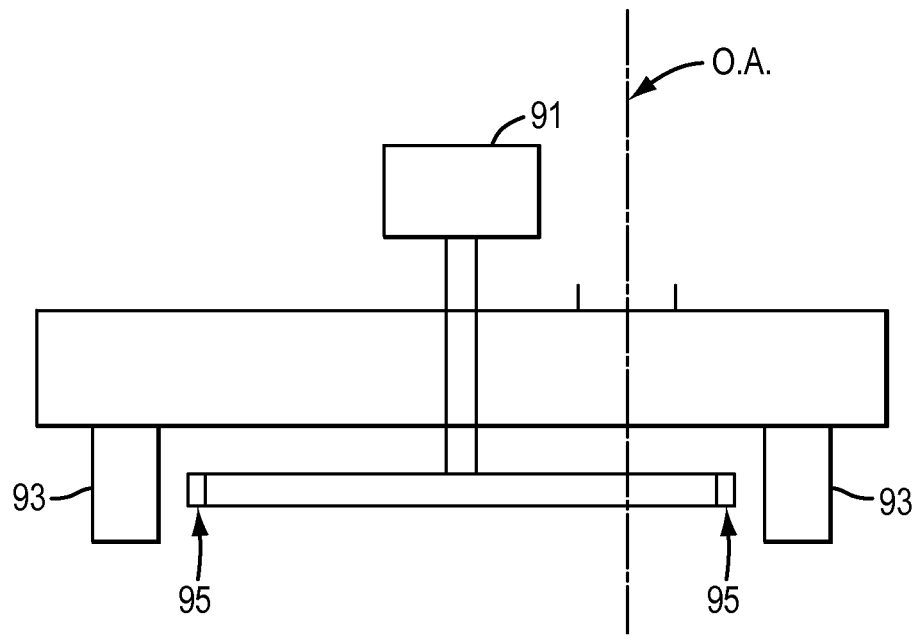
FIG. 11B is one embodiment of the motor.

In some embodiments, as shown in FIG. 11B, the motor can include a rotary position encoder 91 coupled to a magnetic ring (rotor) 95 which is positioned relative to the stator 93. In one embodiment, the optical axis ("O.A.") is located within the diameter of the motor. Torque is produced directly at the outside diameter of the filter wheel and not coupled through the shaft and/or gears. The system's transfer function contains minimal resonances and enables highly dynamic control with minimal settling time and minimal vibration induced into the rest of the system.

Various types of motors can be used such as but not limited to brush type or brushless DC motors, synchronous motors or AC induction motors. Motors can be slotted or slottless. The rotor can contain iron or be ironless. The preferred embodiment uses a brushless DC frameless motor with ironless rotor.

To reduce rotor inertia the rotor assembly can be made from and/or comprise a variety of materials, including but not limited to, titanium or carbon fiber. The filter assembly can also be configured with little or no nonessential material to make it very light.

Figure 12A:
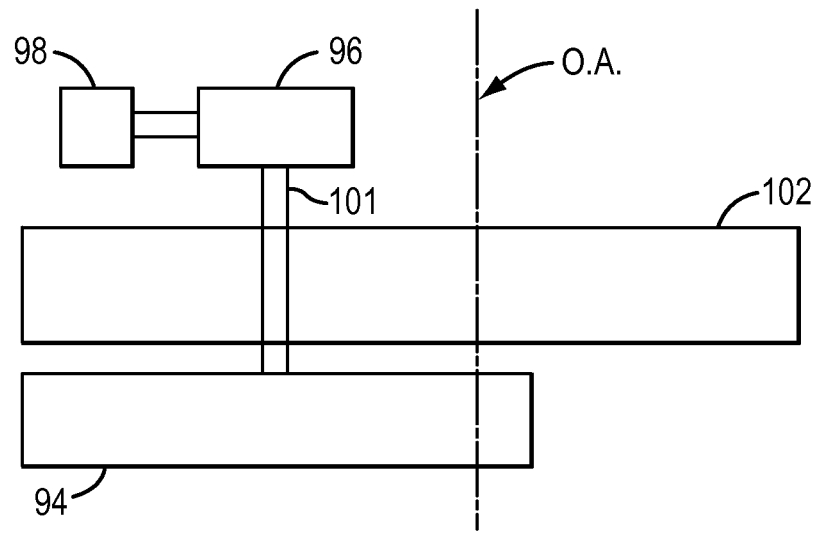
FIG. 12A is a representation of one embodiment of a filter wheel coupled to a motor.
Figure 12B:
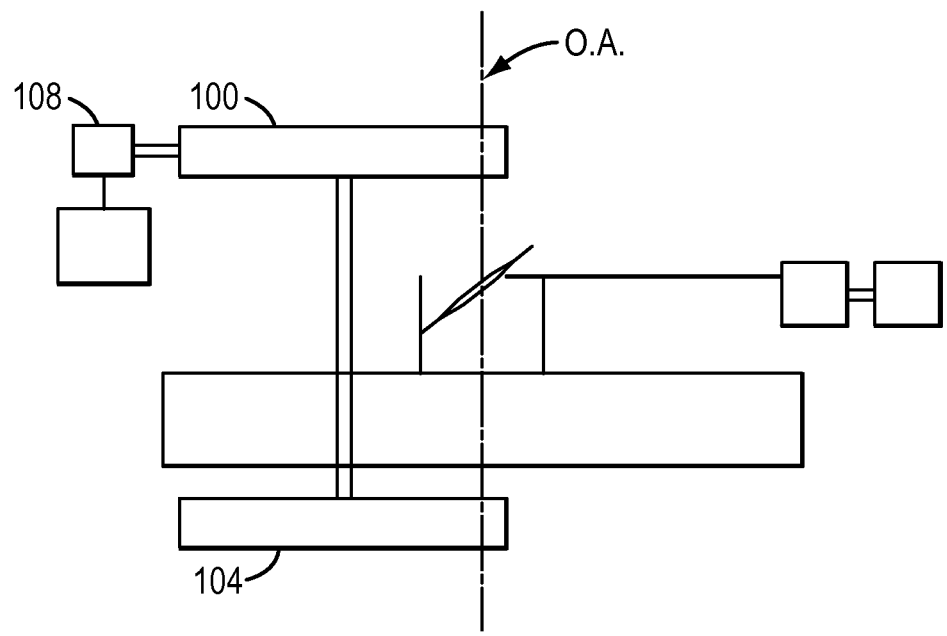
FIG. 12B is a representation of another embodiment of a filter wheel coupled to a motor.
Figure 13:
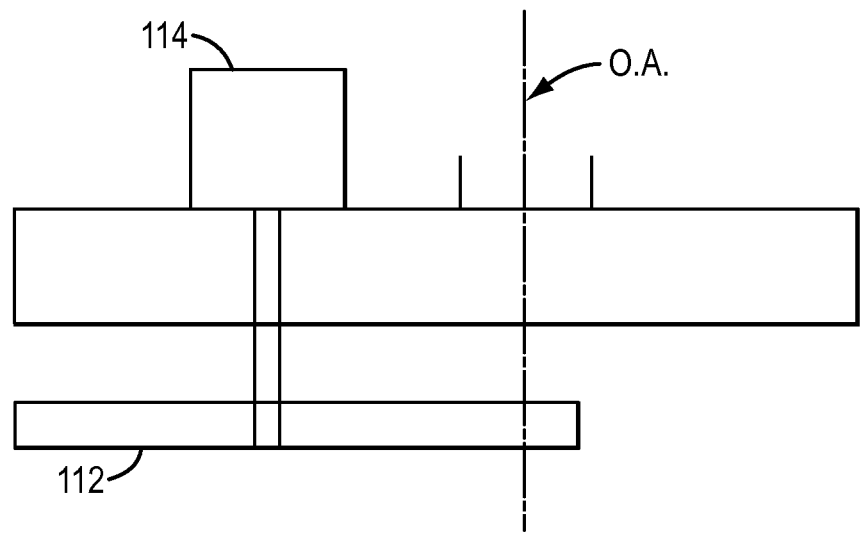
FIG. 13 is a representation of another embodiment of a filter wheel coupled to a motor.

FIGS. 12A, 12B, and 13 provide various alternative embodiments of the mechanics of the filter-wheel 36. For example, FIG. 12A shows a small gear 98 in communication with a large gear 96 while the large gear 96 is mechanically coupled to the filter wheel 94 through a base plate 102 via a shaft 101. As shown, the filter can be rotated such that a discrete area coinciding with a select filter resides within the Optical Axis ("O.A.") to thereby direct filtered light to/from the sample area being imaged. FIG. 12B provides another embodiment having an alternative configuration of a small gear 108 coupled to a large gear 106 coupled to the filter wheel 104. FIG. 13 provides yet another embodiment showing a motor 114 coupled to the filter wheel 112. Those skilled in the art will appreciate that various alternative configurations are within the spirit and scope of the present disclosure.

Various motors are within the spirit and scope of the present disclosure. FIGS. 14A-14F provide speed versus torque graphs for various embodiments of a motor capable of being utilized with some embodiments of the fast-indexing filter wheel.

As the filter wheel indexes between positions, a vibration dampening mechanism may be employed to allow for rapid rotation and stopping, alleviating vibrations which might otherwise be capable of creating issues with sample imaging such as blurring, loss of focus, improper tracking, etc. That is, when the fast-indexing filter wheel is configured to index in approximately 50 ms or less, the system can include an anti-vibration mechanism, detailed further below, which can improve imaging caused by this rapid rotation by minimizing motion of the optics and sample to less than about 1.0 microns in order to avoid image blurring. The vibrations can result in poor quality images and/or may result in diminished analysis timing/speed because the system may be required to slow down in order to allow the vibrations to subside prior to imaging.

In one embodiment, the system can also include a process control step wherein the imaging data can be immediately analyzed to determine if there is a potential error prior to moving onto additional samples, imaging panels, etc. That is, the system can monitor the imaging date generated at each wavelength. If an error (or potential error) has been identified, the system can automatically repeat the analysis at the wavelength in question before moving onto the next imaging area. In other embodiments, the system can be configured to repeat some steps as a process control. For example, the system can repeat some readings at regular intervals in order to generate quality control data. Those skilled in the art will appreciate that various such process control steps are within the spirit and scope of the present disclosure.

Figure 15:
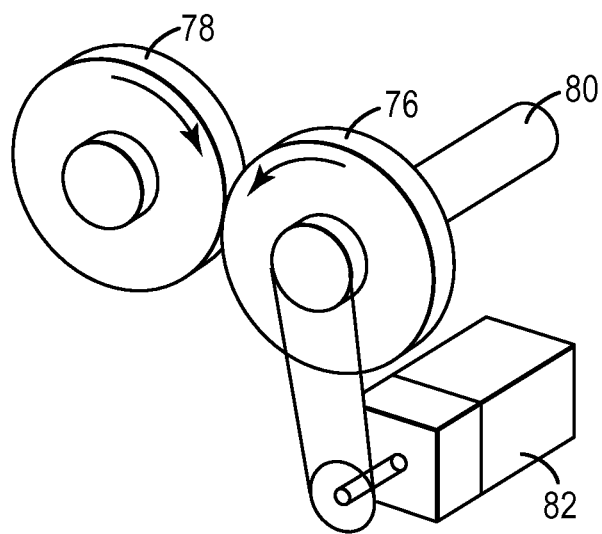
FIG. 15 is a representation of an embodiment of an anti-vibration mechanism coupled to a filter wheel.
Figure 14C:
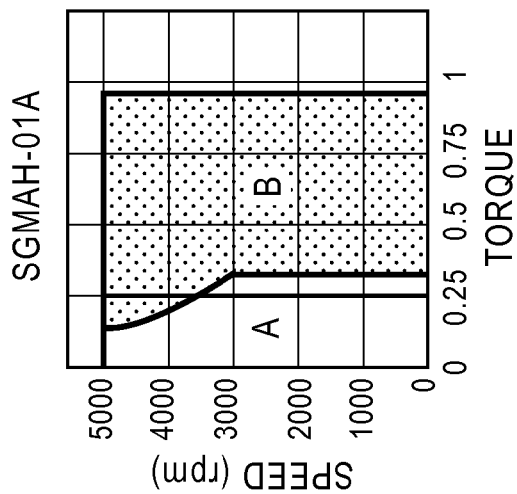
FIG. 14A-FIG. 14F show graphs of speed versus torque for different embodiments of a motor.
Figure 14B:
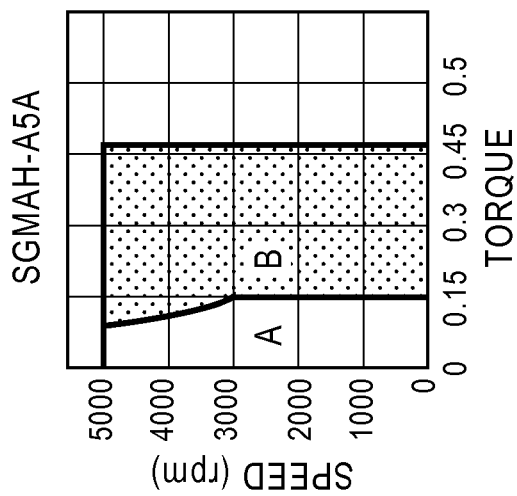
Figure 14A:
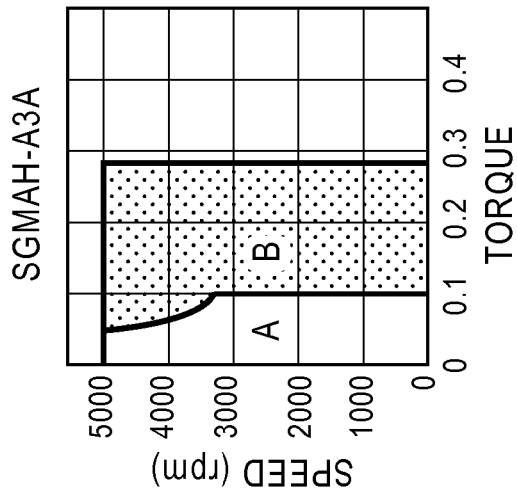
Figure 14F:
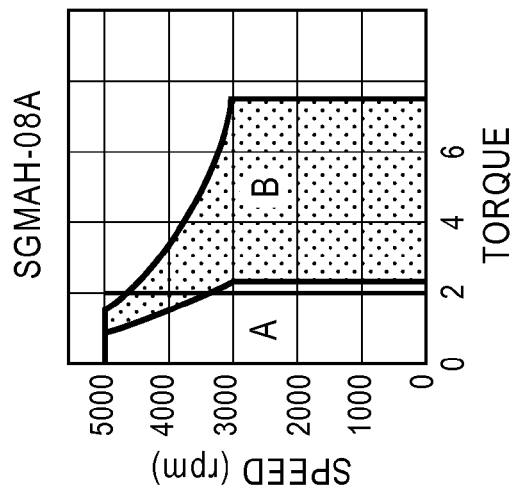
Figure 14E:
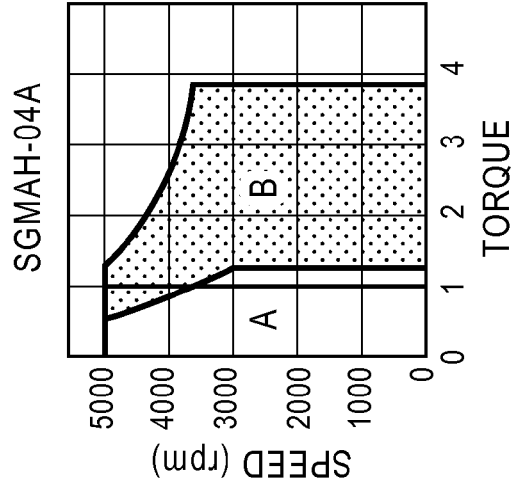
Figure 14D:
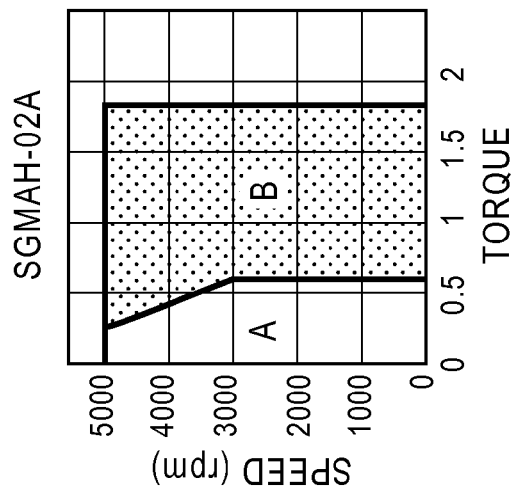

Various embodiments of the presently disclosed system can account for such vibrations. For example, the filter-wheel can be coupled to an anti-vibration mechanism configured to minimize vibrations which may be harmful to imaging and/or analysis. FIG. 15 provides one embodiment of such an anti-vibration mechanism which includes a counterbalance disk 78 coupled to the filter wheel 76. The counterbalance or fly-wheel component 78 can be of approximately equal rotational inertia to the filter-wheel 76, and can be coupled to the filter wheel 76 such that the disk 78 rotates in the opposite direction relative to the filter wheel 76. The orientation of the counterbalance disk 78 and filter wheel 76 allow 2-plane dynamic balancing of vibration caused by rotation of the filter wheel 76. The counterbalance disk 78 can be driven by the friction between the filter wheel 76 and the counterbalance disk 78. Those skilled in the art will appreciate that various alternative embodiments of the counterbalance disk can be coupled to the filter wheel in a variety of manners while remaining within the spirit and scope of the present disclosure.

In other embodiments, as shown in FIGS. 5-8, the fast-indexing filter wheel can be coupled to a stabilization plate 35 which is sized and configured to minimize such vibrations stemming from the fast-indexing filter wheel. Those skilled in the art will appreciate that various other such anti-vibration mechanisms incorporated into the optics/imaging mechanism 20 and/or the fast-indexing filter wheel 36 are within the spirit and scope of the present disclosure.

In addition to those vibrations resulting from rapid starting and stopping of the filter wheel, other sources of vibration can cause imaging issues. That is, due to the small sample size or relative size of features being imaged (e.g., beads having diameters of 1 micron or less), even minor instrument vibrations can affect the speed and/or quality of imaging. Thus, in additional to minimizing vibrations of the fast-indexing filter wheel, various embodiments of the system can also be configured to minimize external vibrations such as those arising from ventilation/air conditioning, foot-traffic, machinery, or operators that might cause image blurring.

Figure 16:
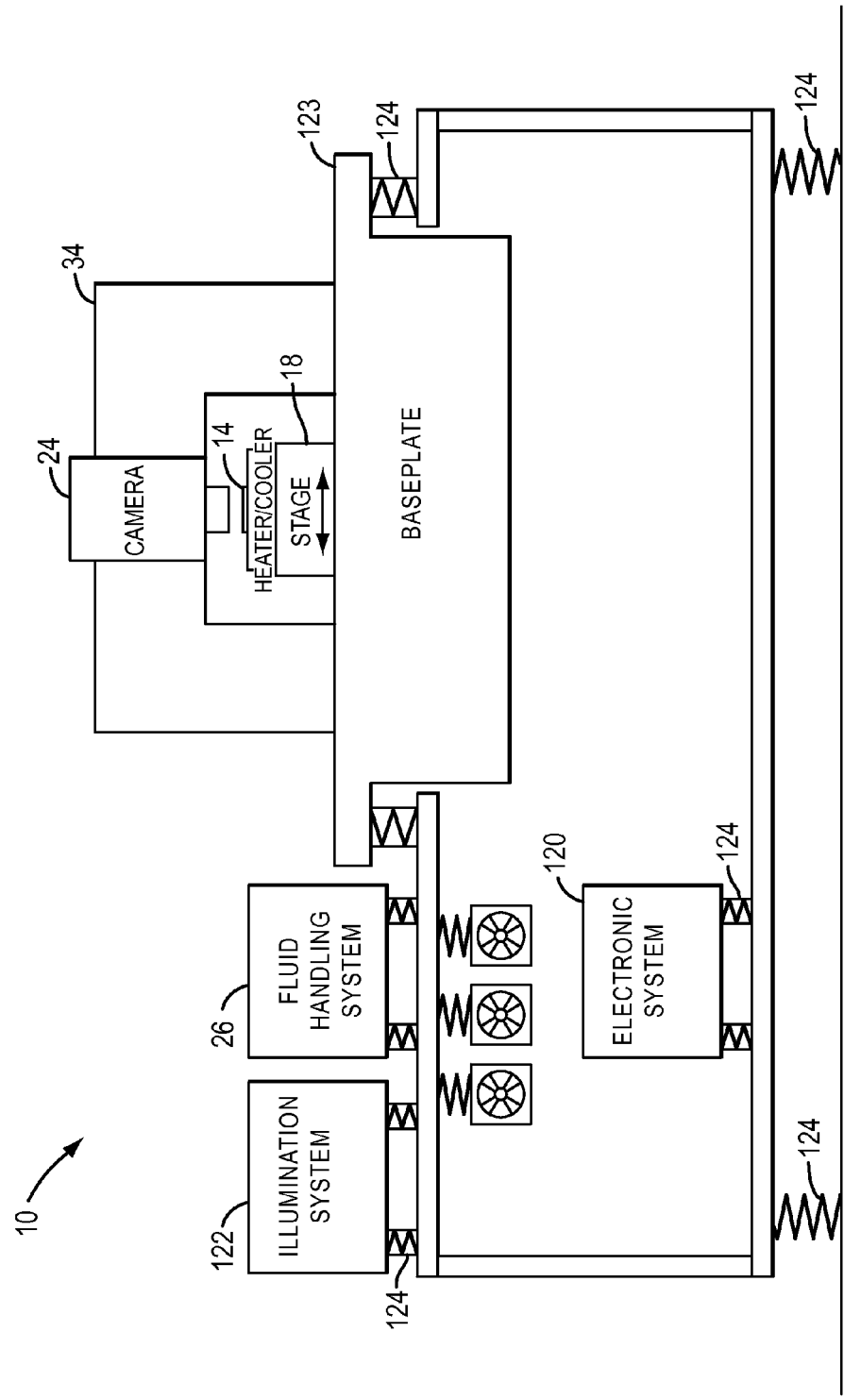
FIG. 16 is a representation of an embodiment of the presently disclosed system wherein various components have been vibrationally isolated from other components.

For example, in one embodiment, various components of the system can be vibrationally isolated from other components. Thus, vibrations generated by one component of the system (e.g., the precision reagent delivery system), will not disturb and/or impact upon the optics/imaging mechanism 20. In one embodiment, as shown in FIG. 16, the system can include a number of vibration isolators 124 disposed at various locations. For example, components such as an illumination system 122, a fluid handling system 26, a baseplate 123, and/or the instrument chassis 127 can be isolated by select positioning of the vibration isolators 124.

In a preferred embodiment, the processing stage 18, optics module 20, and detector 24 can be substantially isolated from the remainder of the system thereby minimizing or at least substantially reducing vibrational effect on imaging. That is, the imaging module 20 and sample stage can essentially be damped or "freely-floating" relative to the remainder of the system. In addition to isolating the baseplate 123, instrument vibrations can also be reduced by removing various vibration sources off the baseplate 123 and onto the instrument chassis 125.

In positioning the vibration isolators 124 relative to the baseplate 123, parameters, such as the center of gravities of the baseplate 123, the stage 18, the sample/flowcell 14, and/or the optics assembly, as well as the height of the baseplate assembly 123 with optics can be considered to provide optimal results. For example, the height of the baseplate assembly 123 can be configured to be of a relatively low profile thereby minimizing rocking (and thus, vibration) of the assembly. Additionally, a high natural frequency of various components on the baseplate 123 can be desirable. Also, components can be mounted on the baseplate 123 with structures that will dampen and/or absorb vibration. For example, granite and concrete structures can absorb more vibration than metal structures such as aluminum.

As also shown in FIG. 16, chassis components can also have vibration isolators 124 on them to help reduce or minimize the amount of vibration being transmitted to the instrument chassis 125. Vibration isolators 124 can also be used between the floor and the chassis 125 to help reduce vibration transmitted therefrom.

Those skilled in the art will appreciate that a wide variety of vibration isolators 124 are within the spirit and scope of the present disclosure. That is, any mechanism capable of providing the required stability while also minimizing vibration can be utilized. In a preferred embodiment, the vibration isolators 124 can be pneumatic isolation systems and/or coiled springs tuned to a low natural frequency to reduce vibration.

In other embodiments, motors capable of driving the processing stage can be selected and/or configured to minimize resulting vibration. For example, there can be less reflected motor inertia and faster move times possible with a direct drive linear actuator compared to an actuator driven by a rotary motor.

Figure 17:
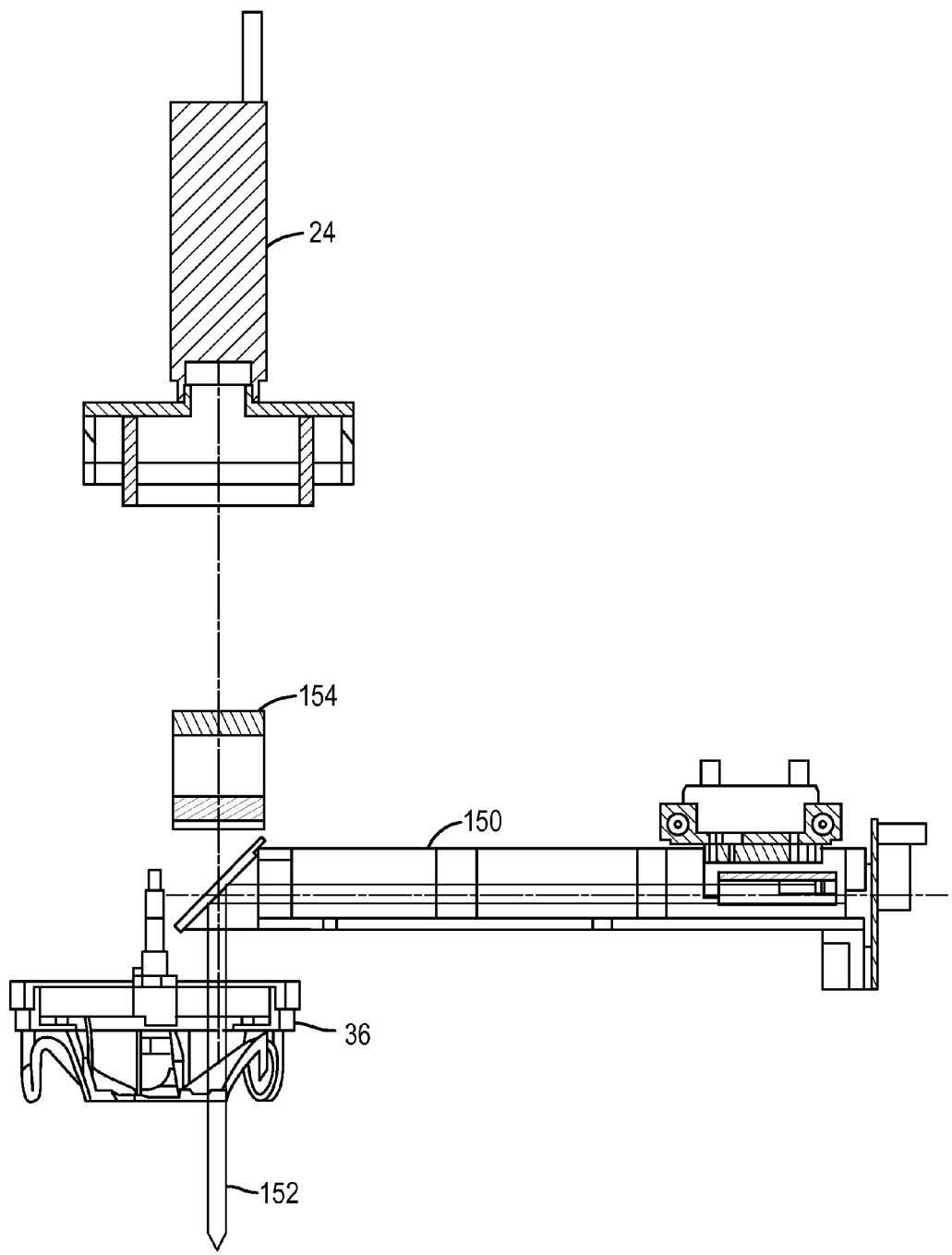
FIG. 17 is a schematic representation of a preferred embodiment of a presently disclosed autofocus system.
Figure 18:
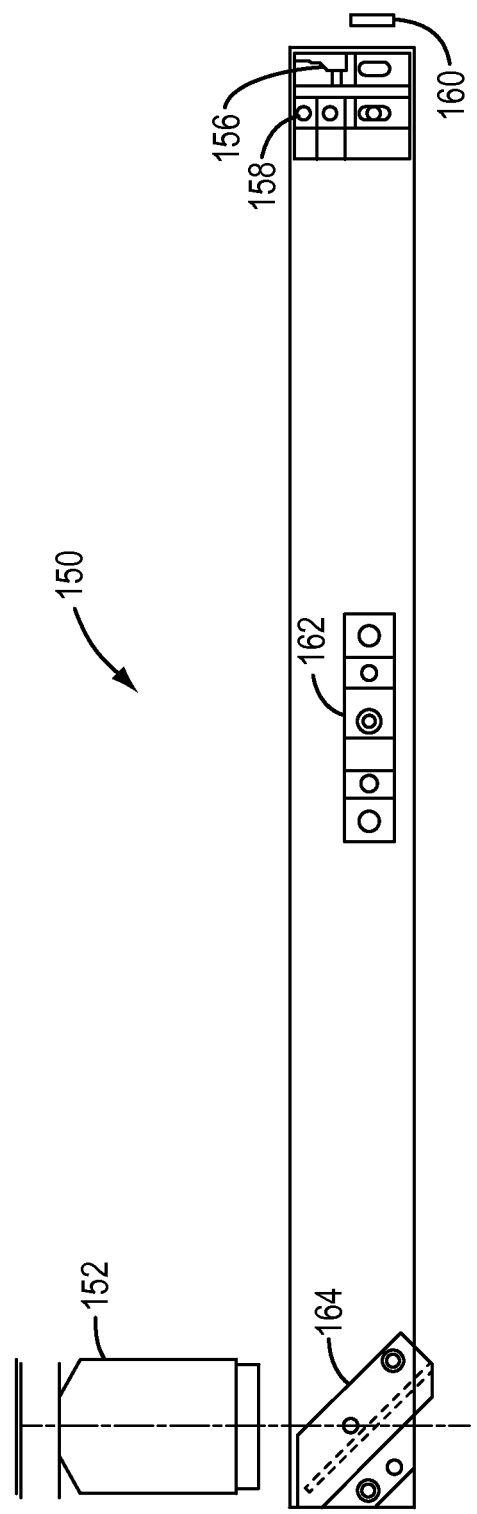
FIG. 18 is another schematic representation of the autofocus system.

In addition to the fast-indexing filter wheel devices and systems described above, the system can also include various embodiments of an auto-focus system capable of automatically monitoring and maintaining the system at best focus. More specifically, as shown in FIGS. 17 and 18, the autofocus system 150 includes a laser 156 configured to project a beam through an outer portion of a clear aperture of the objective 152 and using the convergence of the exit lens to pass the laser through the focal point. FIG. 17 provides one embodiment illustrating the relationship between the system 150 and the fast-indexing filter wheel 36, detector 24, and other system optics (e.g., a tube lens 154). Upon reflecting from a surface near the focal point, the reflected beam reenters the objective 152 at an offset based on how close the reflecting plane was to the objective (within a certain working range of the objective). The laser returns along a path opposite the centerline of the original path to a sensor 160 that determines the offset from the centerline of the laser. An imaging algorithm selects the optimal focus based on best contrast of a focus image stack (images at different Z positions). Best image focus is correlated to the sensor 160 position of the laser 156. Being hardware driven and analog output, the laser autofocus can determine the focus position in real time with continuous output and far faster than an imaging based solution. The only time loss is in digitizing the output and converting into a motion.

FIG. 18 provides a preferred embodiment of the autofocus system 150. As shown, a dichroic element 164 configured to reflect a wavelength of the focus laser 156 (e.g., about 780 nm) is used to access the optical path for the system. In one embodiment, a 780 nm semiconductor laser is focused through a 4 mm diameter PCX lens 158 with 6 mm focal length to collimate the laser beam. The collimated beam is introduced approximately 4 mm off axis from the optical path and close to parallel to enter on the edge of the clear aperture of the objective 152. The return beam from the surface is approximately 4 mm off axis diametrically opposed to the laser path and after passing through various optical components 162 ideally strikes the center of the sensor 160 at best focus. In one embodiment, the sensor 160 is configured as a position sensitive device configured to detect a 6 mm overall travel of the beam.

As described above, for an imaging instrument it can be important to keep the sample as close to optimal (or "best") focus as possible. One way to find best focus is to move the sample plane in the focus direction capturing an image at each possible best focal plane. The standard deviation (contrast) of all pixels in the image will be maximized when the focal plane is at the best focus.

One potential drawback of this method is that it requires numerous images be taken and therefore can be relatively slow. One way to mitigate this problem is to create a map of best focus for each imaging panel prior to beginning a run. This focal map can then be used during the run to establish the best focal plane at each imaging panel location. A potential drawback with this is that because of thermal cycling, the best focus for a given panel can change during a run.

Some embodiments of the presently disclosed system are provided herein which are configured to sense shifts in the best focal plane and accommodate them in real-time during a run. One way to do this is by sending a laser through the imaging objective parallel to the light path but moved off center from the axis of the objective. When the plane of interest is at best focus, the beam will reflect off of it and back into the objective. It will exit the objective parallel to the optical axis. A detector can be placed a distance away and the laser position can be monitored in real time.

When the plane of interest is not at best focus, the laser will exit the objective at an angle relative to the optical axis. This will result in a lateral translation of the beam at the detector, relative to the position of the beam at best focus. The position of the beam can be sensed and focus changed until the beam falls again at the position corresponding to best focus.

One issue with this system is that if the plane of best focus is not exactly perpendicular to the optical axis (e.g. tipped), the beam will still exit the objective parallel to the optical axis. It might, however, undergo a slight translation due to the tip of the plane of best focus. This translation can appear at the detector as if focus was incorrect. If the system moves the sample plane to get the laser back to its original position, it can be at the wrong focus.

Figure 19:
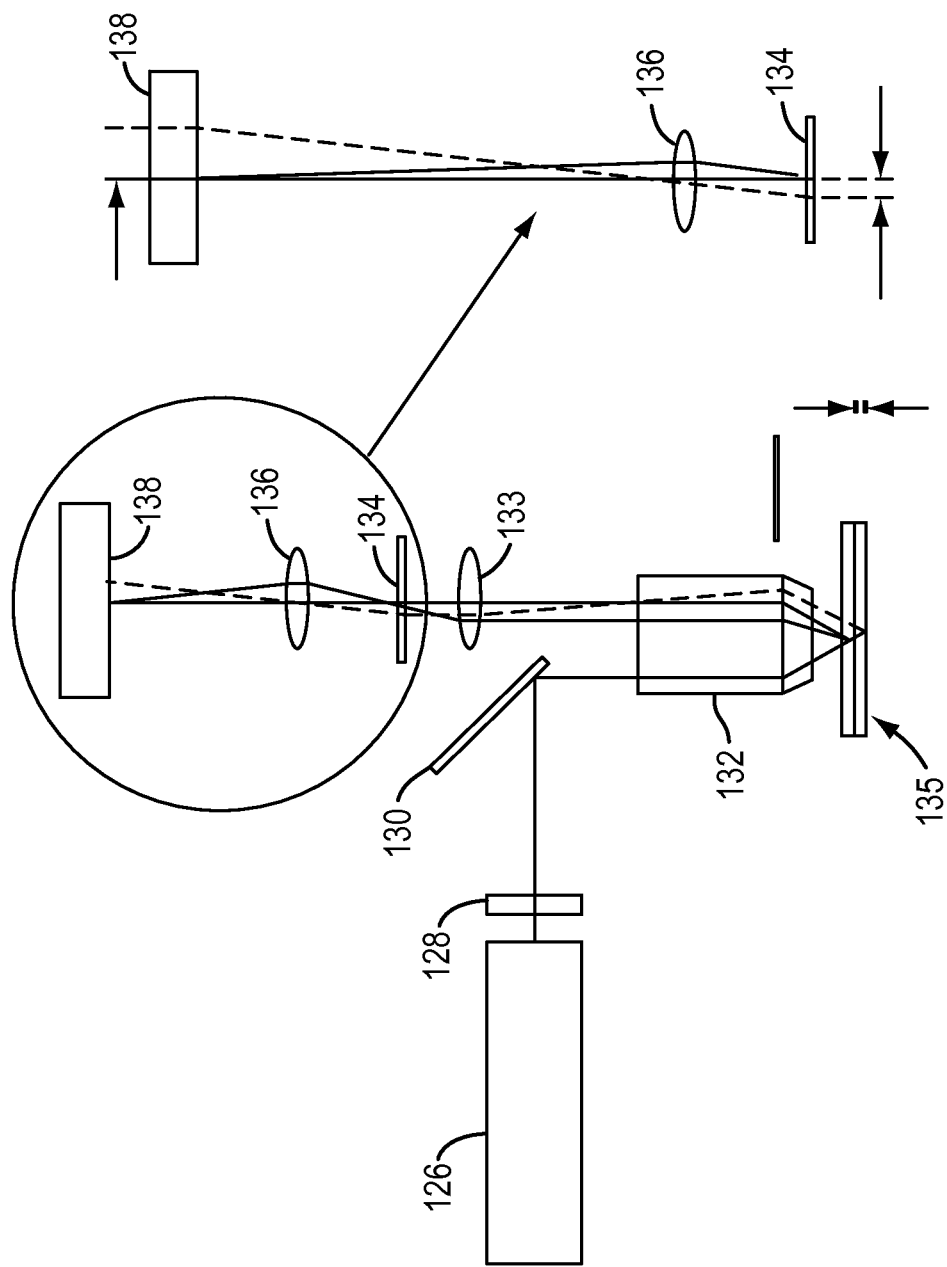
FIG. 19 is a representation of an autofocus with tip-correction algorithm.

In some embodiments, as shown in FIG. 19, the system can further be configured to individually map the best laser position for each region of interest (e.g., each imaging panel) while also being configured to be substantially insensitive to any degree of tip misalignment or articulation in the sample plane. In some embodiments, the system is configured for such tip insensitivity by inserting a focusing lens 133 in the return path of the laser from a source 126 which is focused on the detector 138. All laser beams which have been translated but are parallel to the original optical axis of the system will fall at the focus of the focusing lens 133 and at the same position on the detector 138. Thus a tip in the sample plane will not cause movement of the spot on the detector 138. However, if the laser is at an angle other than the optical axis due to the sample plane not being at best focus, it will be translated on the detector 138. The system can further increase sensitivity by incorporating a magnifying lens 136 which reimages the laser spot onto the detector 138. Sensitivity of the system can be chosen by the placement of this magnifying lens 136.

Referring to FIG. 19, some embodiments of such an off axis real-time laser autofocus system can include a laser 126, preferably infrared, a beam splitter 135 which introduces the laser into the optical path and reflects the laser upon its return from the sample plane through a focusing lens 133. The focal plane 134 of the focusing lens 133 is then reimaged with increased magnification by a magnifying lens 136 onto a detector 138.

The two solid lines in FIG. 19 represent the laser beam when the sample is at best focus and the sample plane is exactly perpendicular the objective and the laser beam at best focus with some tip in the sample plane resulting in some translation due to tip. Both beams are coincident at the focus of the first lens and at the focus of the second lens (i.e., the detector). Hence, the position on the detector 138 is no longer sensitive to tip. The dashed line represents a laser beam when the sample is not at the best focus. It leaves the objective lens at an angle. It is separate from the two solid beams at the focus of the first lens. However, it is still very close so the sensitivity is reduced. After passing through the second lens 136, it is much farther from the two solid beams so the sensitivity has been increased due to the magnification of the second lens 136. At the detector it can now be distinguished from the perfect focus beam and the perfect focus beam with tip.

The laser 126 can be a round TEM00 laser or an astigmatic laser directly from a laser diode. With the beam astigmatic and oriented in the correct direction, the system would be less sensitive to alignment. The laser 126 could be any convenient wavelength. After passing through various optical components (e.g., a filter 128, mirror 130, etc.), it can be introduced into the primary optical path using a beam splitter coated for its wavelength or by a piece of plain glass. It can also be an LED or other light source which has been collimated. The detector 138 can also be a one or two dimensional CCD or CMOS detector or could be a position sensitive detector (PSD). It can also be a linear array of photodiodes. The detector 138 width and magnifying lens 136 position can be selected to give desired dynamic range with maximum sensitivity. The detector 138 height can be selected to minimize alignment difficulties. In addition to the hardware of the system, the present teachings provide a method to minimize difficulty in aligning the system and maximizing speed of the real-time system. This method involves mapping the return laser position on the detector for each imaging panel location when best focus is determined before the run is begun using the contrast (maximum standard deviation) method. The real-time system already knows approximately where best focus is and then only needs to compensate for the small changes of best focus which occur during the run. This method could also be used on a hardware system which does not include the tip compensation portion of the design.

Figure 20:
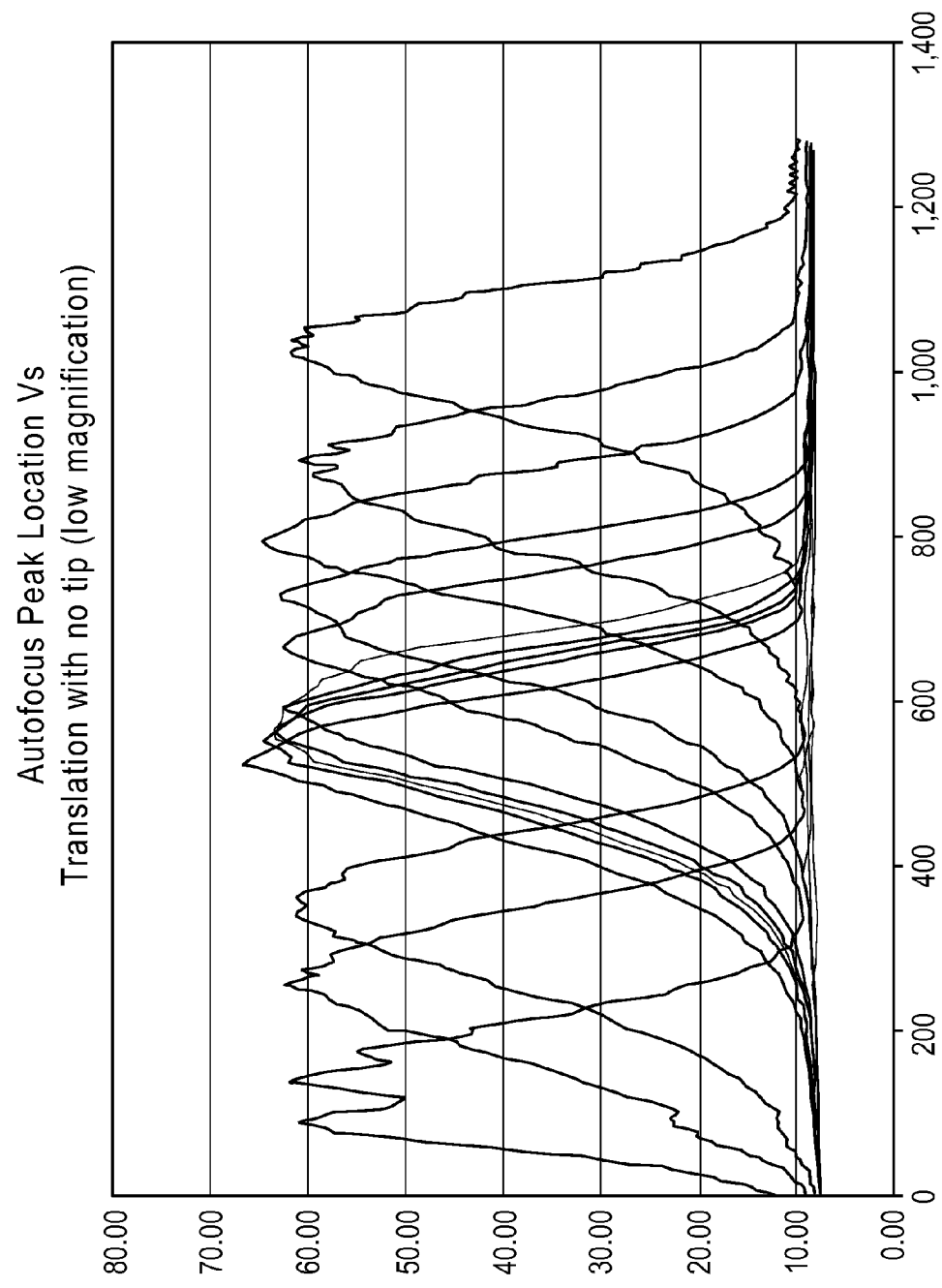
FIG. 20 provides a graph of autofocus peak location versus translation with no tip (low magnification)
Figure 21:
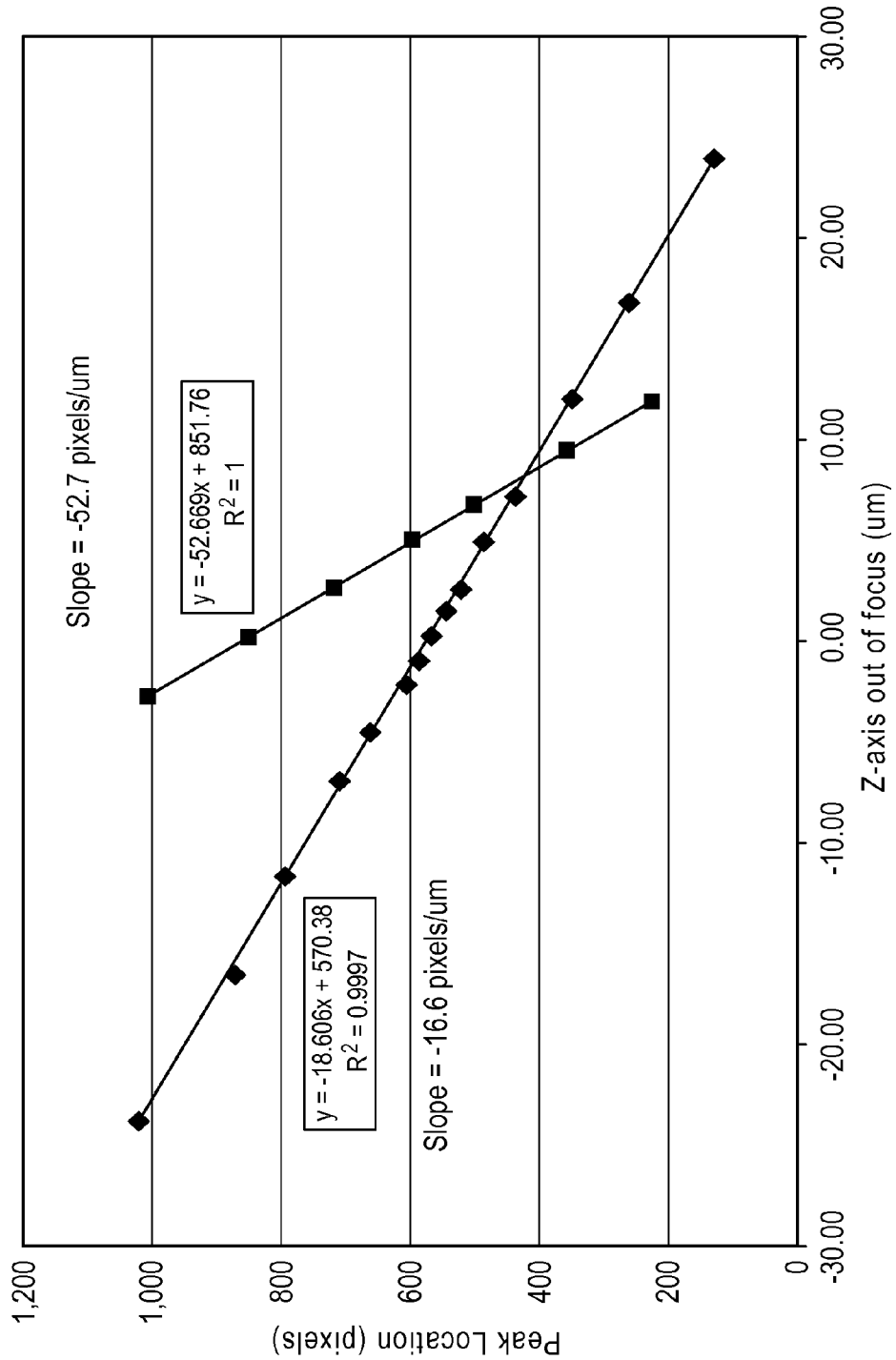
FIG. 21 provides a graph of autofocus z-axis calibration low magnification versus high magnification.

One advantage of this system is that it compensates for errors caused by tip in the sample surface. It also can advantageously speed up a real-time autofocus system by mapping the laser position at best focus prior to beginning the run. Beneficial results from the use of such systems are presented in FIGS. 20-21.

Referring again to FIG. 1, the system can include a controller 30 configured to control various aspects of the system. For example, the controller 30 can control manipulation of the flowcell(s) and the processing stage relative to the optics while also being configured to control the precision reagent delivery mechanism. Further, the controller 30 can be configured to control the fast-indexing filter wheel in relation to the target sample. That is, the controller 30 can be configured to control indexing between filters while also controlling the excitation source. Further, the controller 30 can manipulate the flowcell/processing stage relative to the filter-wheel as the system moves from the analysis of one sample (or imaging panel) to a second sample (or second imaging panel).

Figure 22:
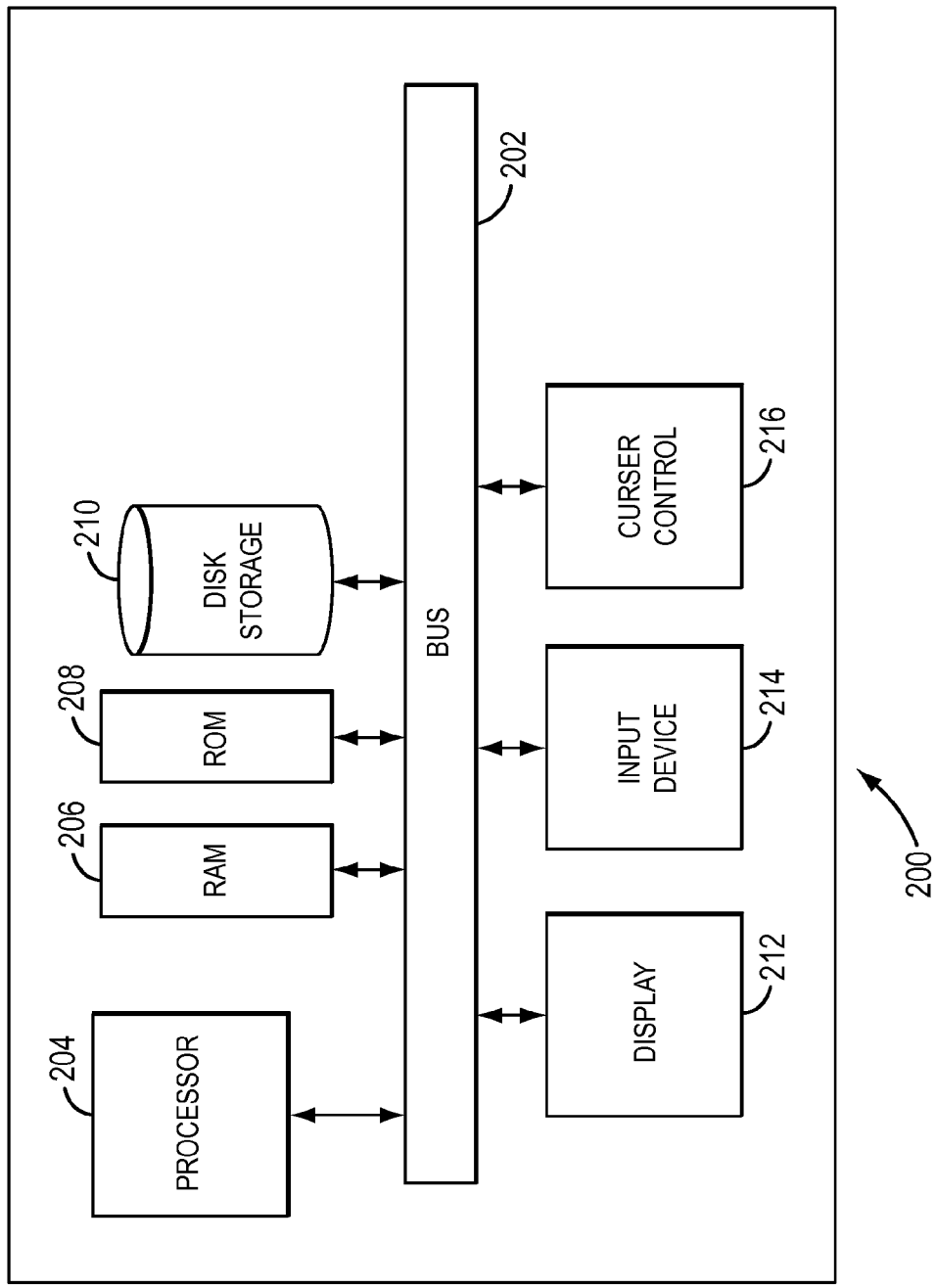
FIG. 22 is a schematic diagram of a preferred embodiment of a presently disclosed computer system.

The controller can include various embodiments of a computer system configured to control the flowcell(s), processing stage, temperature profile, precision reagent delivery mechanism, etc. For example, FIG. 22 is a block diagram that illustrates a computer system 200, upon which embodiments of the present teachings may be implemented. Computer system 200 includes a bus 202 or other communication mechanism for communicating information, and a processor 204 coupled with bus 202 for processing information.

Computer system 200 also includes a memory 206, which can be a random access memory (RAM) or other dynamic storage device, coupled to bus 202 for issuing instructions to be executed by processor 204. Memory 206 also may be used for storing temporary variables or other intermediate information during execution of instructions to be executed by processor 204. Computer system 200 further includes a read only memory (ROM) 208 or other static storage device coupled to bus 202 for storing static information and instructions for processor 204. A storage device 210, such as a magnetic disk, optical disk, EPROM or the like is provided and coupled to bus 202 for storing information and instructions.

Computer system 200 may be coupled via bus 202 to a display 212 (e.g., the user interface 32), such as a cathode ray tube (CRT) or liquid crystal display (LCD), for displaying information to a computer user. An input device 214, including alphanumeric and other keys, touchscreen, etc. may be coupled to bus 202 for communicating information and command selections to processor 204. Another type of user input device is cursor control 216, such as a mouse, a trackball or cursor direction keys for communicating direction information and command selections to processor 204 and for controlling cursor movement on display 212. This input device typically has two degrees of freedom in two axes, a first axis (i.e., x) and a second axis (i.e., y), that allows the device to specify positions in a plane.

A computer system 200 can be implemented in connection with the present teachings for purposes of executed predefined instructions, scripts, or real-time operator issued commands. Consistent with certain implementations of the present teachings, the computer system may perform various operations associated with control, monitoring, and data acquisition to thereby permit automated or semi-automated functionalities. For example, the computer system 200 may be used to invoke and execute desired workflows on the instrument, perform and evaluate instrument diagnostics and operational assessments for the various instrument components, obtain signals and information from the instrument or components thereof, acquire sample data and process results, and output information and data to the user. As will be appreciated by one of skill in the art, information and commands issued and received by the computer system 200 may be in response to processor 204 executing one or more sequences of one or more instructions contained in memory 206. Such instructions may be read into memory 206 from another computer-readable medium, such as storage device 210 or transmitted across a network by another remote computer.

In one exemplary embodiment, execution of the sequences of instructions contained in memory 206 may cause processor 204 to perform the desired operational functionalities including for example, control, monitoring, data acquisition, and data analysis processes. Alternatively hard-wired circuitry may be used in place of or in combination with software instructions to implement the present teachings. Thus implementations of the present teachings are not limited to any specific combination of hardware circuitry and software. Furthermore, computer system 200 may be a remotely located computer or part of a network of computers such as a distributed or cloud computing environment. Furthermore, other electronic devices such as PDAs, cellular phones, laptops or other portable or detached devices may be interconnected with computer system 200 as well as directly or indirectly to the instrument to provide selected functionalities as described above. In various embodiments, these other electronic devices may desirably be used to provide selected functionalities such as monitoring the runtime operation of the instrument, obtaining/downloading sample data, transmitting operations instructions, etc.

The term "computer-readable medium" as used herein refers to any media that participates in providing instructions to processor 204 for execution. Such a medium may take many forms, including but not limited to, non-volatile media, volatile media, and transmission media. Non-volatile media includes, for example, optical or magnetic disks, such as storage device 210. Volatile media includes dynamic memory, such as memory 206. Transmission media includes coaxial cables, copper wire, and fiber optics, including the wires that comprise bus 202.

Common forms of computer-readable media include, for example, a floppy disk, a flexible disk, hard disk, magnetic tape, or any other magnetic medium, a CD-ROM, any other optical medium, punch cards, papertape, any other physical medium with patterns of holes, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 204 for execution. For example, the instructions may initially be carried on the magnetic disk of a remote computer. The remote computer can load the instructions into its dynamic memory and send the instructions over a network or telephone line. A network or modem interface local to computer system 200 can receive the data and convert the data to a signal or format of instructions recognized by the instrument. The instructions may optionally be stored on storage device 210 either before or after execution by processor 204.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

Figure 23:
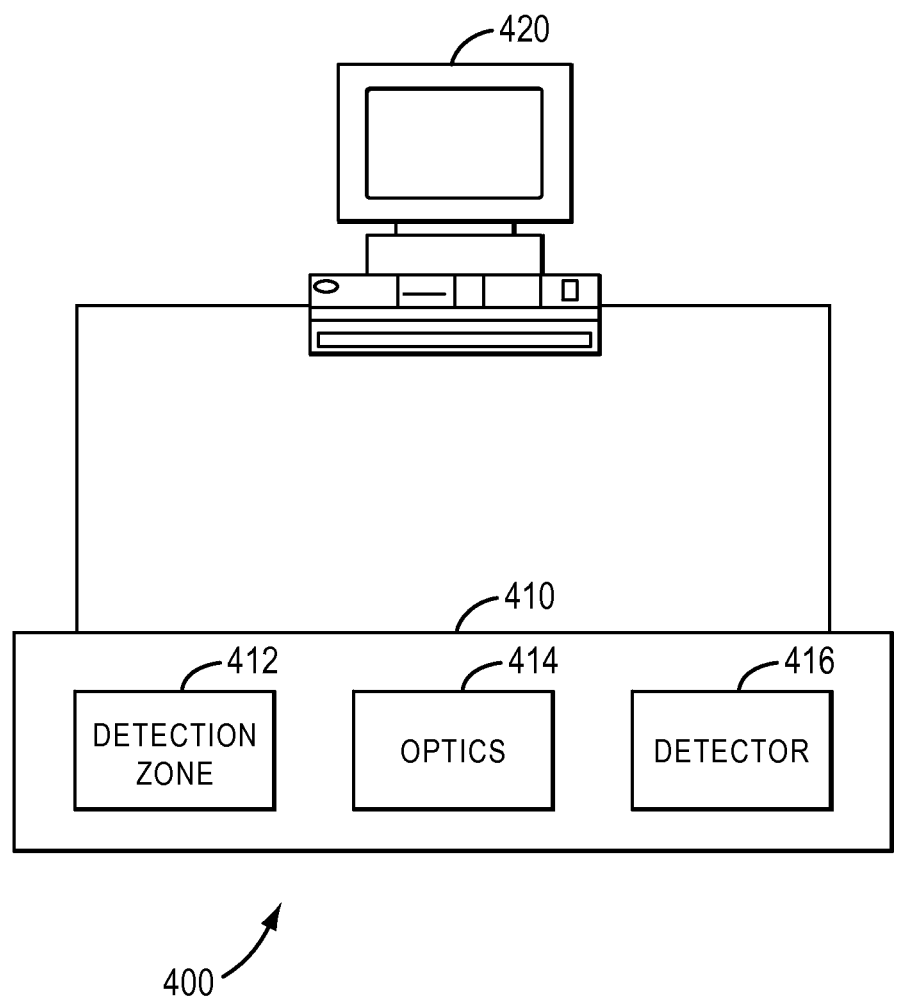
FIG. 23 is a schematic diagram of an embodiment of a system for processing a sample.

FIG. 23 is schematic diagram of a system 400 for processing a sample, in accordance with various embodiments. System 400 includes sample analysis component 410 and processor 420. The sample analysis component 410 can include, but is not limited to including, hardware associated with fluid handling, imaging 412, optics 414, and detector 416. In various embodiments, the sample analysis component may comprise a nucleic acid sequencer 410 such as a next generation DNA sequencing (NGS) system. Nucleic acid sequencer 410 may be capable of interrogating a sample, produces reads from the sample indicative of the composition, and provide the ability to assemble or analyze the data obtained from the instrument.

Processor 420 is in communication with nucleic acid sequencer 410. Processor 420 can be, but is not limited to, a computer, microprocessor, or any device capable of sending and receiving control signals and data from nucleic acid sequencer 410 and processing data. Processor 420 may be configured to perform a number of steps. Processor 420 may obtain the raw data or reads from sequencer 410. Processor 420 may further obtain a reference sequence or genomic information used in further analysis and assembly of the data obtained from the sequencer. In various embodiments, the reference sequence may be retrieved from a database, for example. The database can be a physical storage device with its own processor (not shown) that is connected to processor 420 across a network, or it can be a physical storage device connected directly to processor 420, for example. Processor 420 may be configured to perform selected analysis in addition to the operations/functionalities described above.

In addition to the devices, systems, and computer systems described above, various embodiments of a method for enhancing image quality are also provided herein. For example, in one embodiment, a method of imaging a sample is providing which includes irradiating a sample with excitation energy while rapidly indexing/rotating the fast-indexing filter-wheel. In such an embodiment, the system is capable of imaging a sample or an area of a sample at multiple wavelengths prior to imaging other samples of areas of samples. Once this initial area is imaged at multiple wavelengths, the sample can be moved relative to the optics module/filter wheel such that another sample or another area of the sample can be imaged at multiple wavelengths. These steps can be repeated multiple times such that the entire sample or at least all areas of interest are imaged at multiple wavelengths.

The fast-filter wheel can be configured to index between filters in about 40 ms to about 60 ms, about 45 ms to about 55 ms, etc. In a preferred embodiment, the fast-indexing filter wheel can index between filters in about 50 ms.

One skilled in the art will appreciate further features and advantages of the disclosure based on the above-described embodiments. Accordingly, the disclosure is not to be limited by what has been particularly shown and described, except as indicated by the appended claims. All publications and references cited herein are expressly incorporated herein by reference in their entirety.

What is claimed is:

1. A DNA sequencing system, comprising:
   a processing stage configured to hold a sample chamber or flowcell for a target sample, the target sample comprising a plurality of polynucleotides;
   an excitation source configured to irradiate at least a portion of the target sample;
   a filter wheel having a plurality of filters such that each filter can be placed into optical communication with the excitation source, wherein the plurality of filters includes a plurality of emission filters and a plurality of excitation filters;
   a motor coupled to the filter wheel, and configured to index between filters in an amount of time within a range of about 40 ms to about 60 ms;
   a controller configured to control movement of the processing stage relative to indexing of the filter wheel during use as the system moves from analysis of one portion of the target sample to another portion of the target sample or to a another target sample;
   a detector configured to detect at least one emission from at least a portion of the target sample; and
   a processor configured to determine sequence data relating to at least one of the plurality of polynucleotides.

2. The system of claim 1, wherein the amount of time is about 50 ms.

3. The system of claim 1, wherein the filter wheel includes at least 4 excitation filters.

4. The system of claim 1, wherein the filter wheel includes 5 excitation filters.

5. The system of claim 1, wherein each emission filter is positioned substantially perpendicular relative to one of the plurality of excitation filters.

6. The system of claim 1, wherein the excitation source is an arc lamp.

7. The system of claim 1, wherein the excitation source is a laser.

8. The system of claim 1, wherein an anti-vibration mechanism is coupled to the filter wheel.

9. The system of claim 8, wherein the anti-vibration mechanism is a counter-balance disk.

10. The system of claim 1, wherein a temperature block is in communication with the processing stage.

11. A DNA sequencing system, comprising:
    a processing stage in communication with a temperature block, wherein the temperature block is configured to hold a sample chamber or flowcell for a target sample, the target sample comprising a plurality of polynucleotides;
    an excitation source configured to irradiate at least a portion of the target sample;
    a filter wheel having a plurality of filters such that each filter can be placed into optical communication with the excitation source, wherein the plurality of filters includes a plurality of emission filters and a plurality of excitation filters;
    a motor coupled to the filter wheel, and configured to index between filters in an amount of time within a range of about 40 ms to about 60 ms;
    a controller configured to control movement of the processing stage relative to indexing of the filter wheel during use as the system moves from analysis of one portion of the target sample to another portion of the target sample or to a another target sample;
    a detector configured to detect at least one emission from at least a portion of the target sample; and
    a processor configured to determine sequence data relating to at least one of the plurality of polynucleotides.

12. The system of claim 11, wherein the filter wheel includes at least 4 excitation filters.

13. The system of claim 11, wherein each emission filter is positioned substantially perpendicular relative to one of the plurality of excitation filters.

14. The system of claim 11, wherein the excitation source is an arc lamp.

15. The system of claim 11, wherein the excitation source is a laser.

16. The system of claim 11, wherein an anti-vibration mechanism is coupled to the filter wheel.

17. The system of claim 16, wherein the anti-vibration mechanism is a counter-balance disk.

18. The system of claim 11 further comprising a reagent delivery mechanism in communication with the controller.

19. The system of claim 1 further comprising a reagent delivery mechanism in communication with the controller.

* * * * *